(12) United States Patent
Murray et al.

(10) Patent No.: US 7,744,905 B2
(45) Date of Patent: Jun. 29, 2010

(54) IMMUNOGENIC POLYPEPTIDE ISOLATED FROM MYCOBACTERIUM AVIUM SUBSPECIES PARATUBERCULOSIS AND USES THEREOF

(75) Inventors: Alan Murray, Palmerston North (NZ); Christine Dupont, Ontario (CA)

(73) Assignees: Massey University, Palmerston North (NZ); Institut Pasteur, Paris Cedex (FR)

( * ) Notice: Subject to any disclaimer, the term of this patent is extended or adjusted under 35 U.S.C. 154(b) by 240 days.

(21) Appl. No.: 10/518,432

(22) PCT Filed: Jun. 19, 2003

(86) PCT No.: PCT/NZ03/00125

§ 371 (c)(1),
(2), (4) Date: Aug. 1, 2005

(87) PCT Pub. No.: WO04/000878

PCT Pub. Date: Dec. 31, 2003

(65) Prior Publication Data

US 2006/0210578 A1    Sep. 21, 2006

(30) Foreign Application Priority Data

Jun. 19, 2002    (NZ) ..................... 519667

(51) Int. Cl.
*A61K 39/04*    (2006.01)
*A61K 39/02*    (2006.01)
*C07H 21/02*    (2006.01)
*C07H 21/04*    (2006.01)

(52) U.S. Cl. .............. 424/248.1; 424/9.1; 424/9.2; 424/184.1; 424/234.1; 424/278.1; 424/282.1; 435/69.1; 435/243; 435/253.1; 530/300; 530/350; 536/23.1; 536/23.7

(58) Field of Classification Search ............ 424/9.1, 424/9.2, 184.1, 234.1, 248.1, 278.1, 282.1; 435/69.1, 243, 253.1; 530/300, 350; 536/23.1, 536/23.7
See application file for complete search history.

(56) References Cited

FOREIGN PATENT DOCUMENTS

| WO | WO99/09186 | 2/1999 |
|---|---|---|
| WO | WO00/39301 | 7/2000 |
| WO | WO03/013596 | 2/2003 |

OTHER PUBLICATIONS

Billman-Jacobe et al, Australian Vet Jour, vol. 69, No. 2, pp. 25-28, A comparison of the interferon gamma assay with the. . . .
Chiodini et al, Johne'S Disease, pp. 219-262, 1984, Ruminant Paratuberculosis (Johne's Disease): The Current Status and. . . .
Collins et al, Jour of Clinical Microbiology, vol. 28, No. 7, pp. 1591-1596, Jul. 1990, Identification of Two Groups of. . . .
Cousins et al, Proc of 6th Intl Coll on Paratuberculosis, pp. 259-263, 1999, Investigation of False-Positives in the IS900. . . .
Lepper et al, Australian Vet Jour, vol. 66, No. 2, Feb. 1989, pp. 50-55, Sequential bacteriological observations in relation to. . . .
Koets et al, Vet Immunology & Immunopathology 70, 1999, pp. 105 115, Heat-shock protein-specific T-cell responses in various. . . .
Ridge et al, Australian Vet Jour, vol. 68, No. 8, Aug. 1991, pp. 253-257, Comparison of the Johne's absorbed EIA and the. . . .
Snapper et al, Molecular Microbiology 4(11), 1990, pp. 1911-1919, Isolation and characterization of efficient plasmid. . . .
Stuart et al, Brit Vet J 121, 1965, pp. 289-318, Vaccination Against Johne's Disease in Cattle Exposed to Experimental. . . .
Sweeney et al, J Vet Diagn Invest 7, 1995, pp. 488-493, Evaluation of a commercial enzyme-linked immunosorbent assay for. . . .
Whipple et al, J Vet Diagn Invest 4, 1992, pp. 23-27, Comparison of a commercial DNA probe test and three cultivation. . . .
Valentin-Weigand et al, J Vet Med 39, 1992, pp. 762-766, Protein Antigens Secreted by mcobacterium paratuberculosis.
Merrifield, J Am Soc 85, 1963, pp. 2146-2149, Solid Phase Peptide Synthesis: I. The Synthesis of a Tetrapeptide. . . .
Pearson, Meth in Enzymology, vol. 183, pp. 63-97, 1990, Rapid and Sensitive Sequence Comparison with FASTP and FASTA.
Buck et al, in Vitro, vol. 18, No. 4, Apr. 1982, Monoclonal Antibodies Specific for Cell Culture Mycoplasmas.
Altschul et al, Nucleic Acids Res, vol. 25, No. 17, 1997, pp. 3389-3402, Gapped Blast and PSI-Blast: a new generation of. . . .
Pearson et al, Proc Natl Acad Sci, vol. 85, pp. 2444-2448, Apr. 1988, Improved tools for biological sequence comparison.
Kohler et al, Nature, vol. 256, pp. 495-497, Continuous cultures of fused cells secreting antibody of predefined specificity.
Huse et al, Science, vol. 246, pp. 1275-1281, Dec. 8, 1989, Generation of a Large Combinatorial Library of the. . . .

*Primary Examiner*—Rodney P. Swartz
(74) *Attorney, Agent, or Firm*—Jacobson Holman PLLC

(57) ABSTRACT

The present invention relates to an immunogenic polypeptide isolated from *Mycobacterium avium* subspecies paratuberculosis and variants of the polypeptide. The polypeptide and variants may be used in vaccines against Johne's disease and in methods for detection of the disease. Antibodies against the polypeptide or variants may be used in diagnostic tests for Johne's disease. Also included are polynucleotides encoding the polypeptide and variants, and methods for preparing these.

43 Claims, 19 Drawing Sheets

MQTRRRLSAVFASLTLATALIAGCSSGSKQSGAPLPDPTSLVKQSADATKNVKSVHLVLSIQGKISGLPIKTL
TGDLTTTPATAAKGNATITLGGSDIDANFVVVDGTLYATLTPNKWSDFGKASDIYDVSVLLNPDNGLGNALAN
FSNAKAEGRETINGQSTIRISGNVSADAVNKIMPQFNATQPVPSTVWVQETGDHQLVQANLQKSSGNSVQVTL
SNWGEQVQVTKPPVSS

Figure 1 atgcagacccgccgccgcctatcggccgttttcgcatccctgaccctcgccaccgccttgatcgccggctgct
cgtcgggctccaagcagagcggtgcgccgctgcccgaccccaccagcctggtcaagcagtcggccgacgcgac
caagaacgtcaagagcgtgcacctggtgctcagcatccagggcaagatctccgggctgcccatcaagacgctg
accggtgacctcaccaccacgccggccaccgccgcgaagggcaacgccacgatcaccctgggcggctcggaca
tcgacgccaacttcgtcgtcgtcgacggcaccctgtacgccaccctcaccccgaacaagtggagcgacttcgg
caaggcgtccgacatctacgacgtgtcggtgctgctcaaccccgacaacgggctgggcaacgcgctggcgaac
ttcagcaacgccaaggccgagggccgcgaaaccatcaacggtcagagcacgatccggatcagcgggaacgtct
cggcggacgcggtgaacaagatcatgccgcagttcaacgccacccagccggtgccgagcaccgtgtgggtcca
ggagaccggcgaccaccagctggttcaggccaacctgcagaagagctccgggaattccgtgcaggtgacgctg
tcgaattggggcgagcaggtccaggtcaccaagcccccggtgagctcgtga

SEQUENCE LISTING

<160> NUMBER OF SEQ ID NOS: 9

<210> SEQ ID NO 1
<211> LENGTH: 235
<212> TYPE: PRT
<213> ORGANISM: Mycobacterium avium subspecies paratuberculosis

<400> SEQUENCE: 1

```
Met Gln Thr Arg Arg Arg Leu Ser Ala Val Phe Ala Ser Leu Thr Leu
1               5                   10                  15

Ala Thr Ala Leu Ile Ala Gly Cys Ser Ser Gly Ser Lys Gln Ser Gly
            20                  25                  30

Ala Pro Leu Pro Asp Pro Thr Ser Leu Val Lys Gln Ser Ala Asp Ala
        35                  40                  45
```

```
Thr Lys Asn Val Lys Ser Val His Leu Val Leu Ser Ile Gln Gly Lys
 50                  55                  60

Ile Ser Gly Leu Pro Ile Lys Thr Leu Thr Gly Asp Leu Thr Thr Thr
 65                  70                  75                  80

Pro Ala Thr Ala Ala Lys Gly Asn Ala Thr Ile Thr Leu Gly Gly Ser
                 85                  90                  95

Asp Ile Asp Ala Asn Phe Val Val Val Asp Gly Thr Leu Tyr Ala Thr
                100                 105                 110

Leu Thr Pro Asn Lys Trp Ser Asp Phe Gly Lys Ala Ser Asp Ile Tyr
            115                 120                 125

Asp Val Ser Val Leu Leu Asn Pro Asp Asn Gly Leu Gly Asn Ala Leu
130                 135                 140

Ala Asn Phe Ser Asn Ala Lys Ala Glu Gly Arg Glu Thr Ile Asn Gly
145                 150                 155                 160

Gln Ser Thr Ile Arg Ile Ser Gly Asn Val Ser Ala Asp Ala Val Asn
                165                 170                 175

Lys Ile Met Pro Gln Phe Asn Ala Thr Gln Pro Val Pro Ser Thr Val
            180                 185                 190

Trp Val Gln Glu Thr Gly Asp His Gln Leu Val Gln Ala Asn Leu Gln
        195                 200                 205

Lys Ser Ser Gly Asn Ser Val Gln Val Thr Leu Ser Asn Trp Gly Glu
210                 215                 220

Gln Val Gln Val Thr Lys Pro Pro Val Ser Ser
225                 230                 235

<210> SEQ ID NO 2
<211> LENGTH: 708
<212> TYPE: DNA
<213> ORGANISM: Mycobacterium avium subspecies paratuberculosis

<400> SEQUENCE: 2
atgcagaccc gccgccgcct atcggccgtt ttcgcatccc tgaccctcgc caccgccttg      60
atcgccggct gctcgtcggg ctccaagcag agcggtgcgc cgctgcccga ccccaccagc     120
ctggtcaagc agtcggccga cgcgaccaag aacgtcaaga gcgtgcacct ggtgctcagc     180
atccagggca agatctccgg gctgcccatc aagacgctga ccggtgacct caccaccacg     240
ccggccaccg ccgcgaaggg caacgccacg atcaccctgg gcggctcgga catcgacgcc     300
aacttcgtcg tcgtcgacgg caccctgtac gccaccctca cccgaacaa gtggagcgac     360 ttcggcaagg cgtccgacat ctacgacgtg tcggtgctgc tcaaccccga caacgggctg     420
ggcaacgcgc tggcgaactt cagcaacgcc aaggccgagg gccgcgaaac catcaacggt     480
cagagcacga tccggatcag cgggaacgtc tcggcggacg cggtgaacaa gatcatgccg     540
cagttcaacg ccacccagcc ggtgccgagc accgtgtggg tccaggagac cggcgaccac     600
cagctggttc aggccaacct gcagaagagc tccgggaatt ccgtgcaggt gacgctgtcg     660
aattggggcg agcaggtcca ggtcaccaag ccccggtga gctcgtga                   708

<210> SEQ ID NO 3
<211> LENGTH: 30
<212> TYPE: DNA
<213> ORGANISM: Artificial Sequence
<220> FEATURE:
<223> OTHER INFORMATION: Synthesized

<400> SEQUENCE: 3
```

```
gatgggatcc atgcagaccc gccgccgcct                                30
```

<210> SEQ ID NO 4
<211> LENGTH: 30
<212> TYPE: DNA
<213> ORGANISM: Artificial Sequence
<220> FEATURE:
<223> OTHER INFORMATION: Synthesized

<400> SEQUENCE: 4

```
tgagggtacc cgagctcacc gggggcttgg                                30
```

<210> SEQ ID NO 5
<211> LENGTH: 18
<212> TYPE: DNA
<213> ORGANISM: Artificial Sequence
<220> FEATURE:
<223> OTHER INFORMATION: Synthesized

<400> SEQUENCE: 5

```
tcgcgggact acggtgcc                                             18
```

<210> SEQ ID NO 6
<211> LENGTH: 18
<212> TYPE: DNA
<213> ORGANISM: Artificial Sequence
<220> FEATURE:
<223> OTHER INFORMATION: Synthesized

<400> SEQUENCE: 6

```
tcgaactcgc ccgatccc                                             18
```

<210> SEQ ID NO 7
<211> LENGTH: 6
<212> TYPE: PRT
<213> ORGANISM: Mycobacterium avium subspecies paratuberculosis

<400> SEQUENCE: 7

Leu Ile Ala Gly Cys Ser
1               5

<210> SEQ ID NO 8
<211> LENGTH: 38
<212> TYPE: DNA
<213> ORGANISM: Artificial Sequence
<220> FEATURE:
<223> OTHER INFORMATION: Synthesized

<400> SEQUENCE: 8

```
gggaattcca tatgttgatc gccggctgct cgtcgggc                       38
```

<210> SEQ ID NO 9
<211> LENGTH: 39
<212> TYPE: DNA
<213> ORGANISM: Artificial Sequence
<220> FEATURE:
<223> OTHER INFORMATION: Synthesized

<400> SEQUENCE: 9

```
gggaattcca tatgtcacga gctcaccggg ggcttggtg                      39
```

IMMUNOGENIC POLYPEPTIDE ISOLATED FROM MYCOBACTERIUM AVIUM SUBSPECIES PARATUBERCULOSIS AND USES THEREOF

This is a nationalization of the application PCT/NZ2003/000125, filed Jun. 19, 2003 and published in English.

This invention relates to a protein and compositions which contain it. More particularly, it relates to an exported protein identified in culture filtrate from *Mycobacterium avium* subspecies *paratuberculosis*.

BACKGROUND

Johne's disease (*paratuberculosis*) is a chronic wasting disease of ruminant animals caused by the bacterium *Mycobacterium avium* subspecies *paratuberculosis* (*M. ptb*).

The disease spreads insidiously, with animals becoming infected early in life following ingestion of contaminated milk, collostrum, or pasture. In many countries, including New Zealand and the USA, herds are not routinely tested for *M. ptb* infection. The number of herds officially known to have infection is therefore thought to be a gross underestimate of the actual level of infection. Estimates suggest that approximately 60% of dairy herds in New Zealand are infected with *M. ptb*. In sheep, prevalence of *M. ptb* infection may be as high as 70%.

Infected animals are less productive, which results in significant economic losses for farmers. The cost to New Zealand farmers is estimated to be in excess of $30 million per annum. The economic impact in the USA was estimated to be as much as US$1.7 billion per annum (Chiodini et al., 1984a).

Good management practices, herd testing, and culling of infected animals are important tools for controlling *paratuberculosis*. However, this strategy alone is unlikely to completely control the problem because current diagnostic tests frequently fail to identify infected animals in the early, preclinical stages of disease. The early stages of disease are asymptomatic and shedding of the organism in the faeces is undetectable or intermittent. Only animals which progress to the terminal stage generally show clinical disease, and that only after two to five years (Stuart, 1965; Lepper et al., 1989). For this reason, it is suggested that for every clinical case on a farm, there are approximately 20 additional infected animals.

Detection of infection in the host is influenced by the stage of disease (Ridge et al., 1991; Sweeney et al., 1995). In the lengthy preclinical stage, the bacterium produces little or no detectable immune response and the number of organisms is typically low, making direct detection of the bacterium difficult. In cattle, culture of *M. ptb* from faeces or tissue is currently the most accurate means of detecting infection. The success of culture is linked to the presence of sufficient numbers of *M. ptb* being shed from the intestine. Hence, animals in the early stages of disease, which do not shed the bacterium, or shed intermittently, are difficult to detect by this method. A further disadvantage of culture is the long incubation time required for the appearance of colonies.

Serological testing is also available, however, this performs best in animals with clinical disease (80% detection) and poorly with preclinically infected animals (as low as 15% detection), (Billman-Jacobe et al., 1992; Sweeney et al., 1995).

Alternatively, *M. ptb* can be confirmed through PCR to identify the presence of the species-specific DNA fragments. To date, only three subspecies-specific DNA fragments have been identified in the *M. ptb* genome.

Of these, the most widely used is the IS900 element. IS900 detection by PCR is available as a commercial kit (Idexx, USA). This test is reported to have a sensitivity of approximately 60% in infected cattle, based on cattle diagnosed by faecal culture (Whipple et al., 1992). A report of finding organisms that give positive results with IS900 PCR but are not *M. ptb* has placed some doubt on the routine use of this test as the ultimate confirmation of *M. ptb* (Cousins et al., 1999).

Eradication of Johne's disease is difficult due to the inability of current diagnostic tests to detect all infected animals. As a consequence, more animals are put at risk of infection because preclinically infected animals intermittently shed the bacterium, thereby spreading the organism. Therefore, improvements in the sensitivity of diagnostic testing and/or increased immunity of uninfected animals would be beneficial.

Commercially available vaccines for the control of Johne's disease contain whole organisms, either attenuated strains of *M. ptb* (eg. Neoparasec—Merial, France), or heat-killed preparations (eg. Gudair—CZ Veterinaria, Porrino, Spain), which are mixed with an oily adjuvant and injected subcutaneously. Vaccination does not prevent or eliminate infection, but reduces the number of animals that progress to clinical disease and the excretion of organisms in the faeces.

Unfortunately, these whole cell vaccines come with a number of drawbacks. Firstly, the immunogenic load presented by the whole cell in conjunction with the adjuvant induces a severe hypersensitivity reaction at the injection site, which can cause the formation of a persistent nodule (granuloma). Occasional rupture of the nodule causes suffering to the animal and potential downgrading of the carcass at slaughter, with concomitant diminished returns for the farmer. Histological examination of nodules or regional lymph nodes can reveal the presence of acid-fast organisms that can be confused with the tuberculosis organism. Additionally, while Johne's disease is distinct from tuberculosis, and caused by a distinct organism, the current Johne's vaccines can generate cross-reactive responses to *M. bovis* skin test antigens which can interfere with tuberculosis control programmes.

Accordingly, there is a need for alternative methods for detecting Johne's disease in animals, and proteins and/or markers and/or vaccines useful in such methods.

The applicants have identified and characterized a novel protein, from *M. ptb*, which exhibits strong potential as a diagnostic marker and a subunit vaccine. A raw nucleotide sequence similar to that encoding the protein of the invention was located in the TIGR *Mycobacterium avium* subspecies avium database. This nucleotide database was unannotated, the sequence had not been identified as an open reading fame, nor as a gene, and no protein-encoding utility had been ascribed to the raw nucleotide sequence. Accordingly, the applicants are the first to teach the identification of this nucleotide sequence as a protein-encoding gene. The protein can be readily obtained from a culture filtrate of *M. ptb*, or expressed in a heterologous host, as the gene encoding this protein has also been identified and characterized by the applicants. It is towards this protein that the present invention is broadly directed.

SUMMARY OF THE INVENTION

Accordingly, in a first aspect the present invention provides a recombinant, purified, or isolated polypeptide which has a) the amino acid sequence set forth in FIG. 1 (SEQ ID NO:1), or b) a functionally equivalent variant which has greater than 77% amino acid sequence identity with said polypeptide, or c) a functionally equivalent fragment of a polypeptide defined in a) or b).

Accordingly, in another aspect the present invention provides a recombinant, purified, or isolated polypeptide has a) the amino acid sequence of amino acids 20 to 235 as set forth in FIG. 1 (SEQ ID NO:1), or b) a functionally equivalent variant which has greater than 77% amino acid sequence identity with said polypeptide, or c) a functionally equivalent fragment of a polypeptide defined in a) or b).

Accordingly, in another aspect the present invention provides a polypeptide or functionally equivalent valiant, or functionally equivalent fragment as defined above which is obtainable from a bacterium.

Accordingly, in another aspect the present invention provides a polypeptide or functionally equivalent variant, or functionally equivalent fragment as defined above which is obtainable from *Mycobacterium avium* subspecies *paratuberculosis*.

Accordingly, in another aspect the present invention provides a polypeptide or functionally equivalent variant, or functionally equivalent fragment as defined above which is obtainable from *Mycobacterium avium* subspecies *paratuberculosis* ATCC 53950.

Accordingly, in another aspect the present invention provides a polypeptide as defined above which is obtainable from a heterologous host transformed with a polynucleotide which encodes said protein or functionally equivalent variant or fragment thereof wherein said host is capable of expressing said polypeptide.

Preferably, the host is *E. coli*.

Accordingly, in another aspect the present invention provides a recombinant, purified, or isolated polynucleotide comprising the sequence set forth in FIG. 2 (SEQ ID NO:2) or a fragment or variant thereof capable of encoding a polypeptide which has a) the amino acid sequence set forth in FIG. 1 (SEQ ID NO: 1), or b) a functionally equivalent variant which has greater than 77% amino acid sequence identity with said polypeptide, or c) a functionally equivalent fragment of a polypeptide defined in a) or b).

Accordingly, in another aspect the present invention provides a genetic construct comprising (a) a promoter sequence; (b) an open reading frame polynucleotide encoding a polypeptide as defined above; (c) a termination sequence.

Accordingly, in another aspect the present invention provides a recombinant, purified, or isolated polynucleotide comprising the sequence of SEQ ID NO:2 or a variant thereof encoding either the polypeptide comprising the amino acid sequence of SEQ ID NO:1 or a functionally equivalent fragment of said polynucleotide.

Accordingly, in another aspect the present invention provides a recombinant, purified or isolated polynucleotide with a nucleotide sequence complementary to the polynucleotide defined above.

Accordingly, in another aspect the present invention provides one or more oligonucleotide or polynucleotide primers capable of amplifying a polynucleotide which encodes a polypeptide as defined above in a Polymerase Chain Reaction or other polynucleotide amplification method.

Accordingly, in another aspect the present invention provides one or more oligonucleotide or polynucleotide primers capable of amplifying a polynucleotide which encodes a polypeptide which has a) the amino acid sequence set forth in FIG. 1 (SEQ ID NO:1), or b) a functionally equivalent variant which has greater than 77% amino acid sequence identity with said polypeptide, or c) a functionally equivalent fragment of a polypeptide defined in a) or b), in a Polymerase Chain Reaction or other polynucleotide amplification method.

Accordingly, in another aspect the present invention provides a purified or isolated antibody capable of binding a polypeptide as defined above. The antibody may be monoclonal or polyclonal or a recombinant antibody.

In a related aspect, antibodies used in methods of the invention may be present in an antiserum.

Accordingly, in another aspect the present invention provides any isolated or purified antibody capable of binding a polypeptide which has a) the amino acid sequence set forth in FIG. 1 (SEQ ID NO:1), or b) a functionally equivalent variant which has greater than 77% amino acid sequence identity with said polypeptide, or c) a functionally equivalent fragment of a polypeptide defined in a) or b).

Accordingly, in another aspect the present invention provides a composition comprising a polypeptide or functionally equivalent variant or fragment thereof of the invention together with an acceptable diluent, carrier, excipient, or adjuvant, said polypeptide being present in an amount sufficient to generate a protective immune response to *Mycobacterium avium* subspecies *paratuberculosis* infection, said composition suitable for use as a vaccine.

Accordingly, in another aspect the present invention provides a composition which comprises a polypeptide which has a) the amino acid sequence set forth in FIG. 1 (SEQ ID NO:1), or b) a functionally equivalent variant which has greater than 77% amino acid sequence identity with said polypeptide, or c) a functionally equivalent fragment of a polypeptide defined in a) or b).

Accordingly, in another aspect the present invention provides a diagnostic composition comprising a polypeptide of the invention wherein the composition is a component in an assay.

Accordingly, in another aspect the present invention provides a diagnostic composition as defined above wherein the composition is a component is an assay and wherein the assay is capable of detecting the presence of *Mycobacterium avium* subspecies *paratuberculosis*.

Accordingly, in another aspect the present invention provides a diagnostic composition as defined above wherein the composition is a component is an assay and wherein the assay is capable of detecting the presence of *Mycobacterium avium* subspecies *paratuberculosis* at a preclinical phase of Johne's disease.

Accordingly, in another aspect the present invention provides a diagnostic composition as defined above wherein the composition is a component of an assay kit.

Accordingly, in another aspect the present invention provides a composition comprising the polynucleotide comprising the sequence set forth in FIG. 2 (SEQ ID NO:2) or a fragment or variant thereof capable of encoding a polypeptide having greater than 77% amino acid sequence identity with the protein encoded by the polynucleotide comprising the sequence set forth in FIG. 2 (SEQ ID NO:2).

Accordingly, in another aspect the present invention provides a diagnostic composition comprising a polynucleotide of the invention wherein the composition is a component in an assay.

Accordingly, in another aspect the present invention provides a diagnostic composition as defined above wherein the composition is a component is an assay and wherein the assay is capable of detecting the presence of *Mycobacterium avium* subspecies *paratuberculosis*.

Accordingly, in another aspect the present invention provides a diagnostic composition as defined above wherein the composition is a component is an assay and wherein the assay is capable of detecting the presence of *Mycobacterium avium* subspecies *paratuberculosis* at a preclinical phase of Johne's disease.

Accordingly, in another aspect the present invention provides a diagnostic composition defined as above wherein the composition is a component of an assay kit.

Accordingly, in another aspect the present invention provides a composition comprising at least one oligonucleotide or polynucleotide primer capable of amplifying a polynucleotide which encodes a polypeptide which has the amino acid sequence set forth in FIG. 1 (SEQ ID NO:1) or a functionally equivalent variant or fragment thereof which has greater than 77% amino acid sequence identity with said polypeptide, in a Polymerase Chain Reaction or other polynucleotide amplification method.

Accordingly, in another aspect the present invention provides a diagnostic composition comprising a primer of the invention wherein the composition is a component in an assay.

Accordingly, in another aspect the present invention provides a diagnostic composition as defined above wherein the composition is a component is an assay and wherein the assay is capable of detecting the presence of *Mycobacterium avium* subspecies *paratuberculosis*.

Accordingly, in another aspect the present invention provides a diagnostic composition as defined above wherein the composition is a component is an assay and wherein the assay is capable of detecting the presence of *Mycobacterium avium* subspecies *paratuberculosis* at a preclinical phase of Johne's disease.

Accordingly, in another aspect the present invention provides a diagnostic composition as defined above wherein the composition is a component of an assay kit.

Accordingly, in another aspect the present invention provides a composition comprising an antibody capable of binding a polypeptide which has a) the amino acid sequence set forth in FIG. 1 (SEQ ID NO:1), or b) a functionally equivalent variant which has greater than 77% amino acid sequence identity with said polypeptide, or c) a functionally equivalent fragment of a polypeptide defined in a) or b).

Accordingly, in another aspect the present invention provides a diagnostic composition comprising an antibody as defined above wherein the composition is a component in an assay.

Accordingly, in another aspect the present invention provides a diagnostic composition as defined above wherein the composition is a component is an assay and wherein the assay is capable of detecting the presence of *Mycobacterium avium* subspecies *paratuberculosis*.

Accordingly, in another aspect the present invention provides a diagnostic composition defined as above wherein the composition is a component is an assay and wherein the assay is capable of detecting the presence of *Mycobacterium avium* subspecies *paratuberculosis* at a preclinical phase of Johne's disease.

Accordingly, in another aspect the present invention provides a diagnostic composition as defined above wherein the composition is a component of an assay kit.

Accordingly, in another aspect the present invention provides a method of detecting Johne's disease including preclinical Johne's disease in an animal comprising contacting a sample with a polypeptide of the invention or a composition comprising a polypeptide of the invention and detecting a response indicative of the presence of *Mycobacterium avium* subspecies *paratuberculosis*.

Accordingly, in another aspect the present invention provides a method which comprises contacting an animal or a sample from an animal with a polypeptide of the invention or a composition comprising a polypeptide of the invention and detecting a delayed-type hypersensitivity response.

Accordingly, in another aspect the present invention provides a method which comprises contacting a sample with a protein of the invention or a composition comprising a polypeptide of the invention and detecting in the sample the presence of antibodies that bind a polypeptide of the invention.

Accordingly, in another aspect the present invention provides a method wherein the detection of the presence of antibodies is by immunoassay.

Accordingly, in another aspect the present invention provides a method wherein the detection of the presence of antibodies is by ELISA, radioimmunoassay-assay, or Western Blot.

Accordingly, in another aspect the present invention provides a method of detecting Johne's disease including preclinical Johne's disease in an animal comprising contacting a sample with antibody that binds a polypeptide of the invention or a composition comprising said antibody and detecting the presence of said bound antibody.

Accordingly, in another aspect the present invention provides a method wherein the presence of bound antibody is determined by immunoassay.

Accordingly, in another aspect the present invention provides a method wherein the presence of bound antibody and/or ligand is determined by ELISA, radioimmunoassay, or Western blot Accordingly, in another aspect the present invention provides a method which is capable of detecting the presence of *Mycobacterium avium* subspecies *paratuberculosis* at a preclinical phase of Johne's disease.

Accordingly, in another aspect the present invention provides a method of detecting Johne's disease including preclinical Johne's disease in an animal comprising contacting a sample with a composition comprising of at least one oligonucleotide or polynucleotide primers capable of amplifying a polynucleotide which encodes a polypeptide of the invention in a Polymerase Chain Reaction or other polynucleotide amplification method.

Accordingly, in another aspect the present invention provides a method of detecting Johne's disease including preclinical Johne's disease in an animal comprising contacting a sample with a composition comprising a polynucleotide capable of binding to a polynucleotide which encodes a polypeptide of the invention, and detecting said binding.

Accordingly, in another aspect the present invention provides a method wherein said polynucleotide capable of binding to a polynucleotide which encodes a polypeptide of the invention is detectably labeled.

Accordingly, in another aspect the present invention provides a method wherein said detectable label is a radioisotope or fluorescent tag.

Preferably, in any of the methods described above, said animal is a ruminant. More preferably, said animal is a sheep.

Accordingly, in another aspect the present invention provides a method of prophylactically or therapeutically treating an animal against Johne's disease.

Accordingly, in another aspect the present invention provides a method which comprises administering to an animal a polypeptide of the invention or functional variant or fragment thereof and/or a prophylactic or therapeutic composition comprising said polypeptide of the invention or functional variant or fragment thereof, to engender in the animal a protective immunological response.

Accordingly, in another aspect the present invention provides a method which comprises administering to an animal a polypeptide of the invention or functional variant or fragment thereof and/or a therapeutic composition comprising said polypeptide of the invention or functional variant or fragment thereof, to engender in the animal a protective response.

Accordingly, in another aspect the present invention provides a method wherein the prophylactic method comprises administering to said animal a vaccine composition comprising an acceptable diluent, carrier, excipient, or adjuvant, in addition to an immunologically protective amount of a polypeptide of the invention or functionally equivalent variant or fragment thereof, in an amount sufficient to produce a protective response.

Accordingly, in another aspect the present invention provides a method wherein said administration is performed on a single occasion.

Accordingly, in another aspect the present invention provides a method wherein said administration is performed on more than one occasion.

Preferably, the amount of polypeptide administered lies in the range of 0.1-1000 μg/kg.

Preferably, the amount of polypeptide administered lies in the range of 5-5000 μg/kg Preferably, in any of the methods described above said animal is a ruminant. More preferably, said animal is a sheep.

Accordingly, in another aspect the present invention provides a kit for use in detecting the presence of *Mycobacterium avium* subspecies *paratuberculosis* comprising at least two of the following: a) a polypeptide of the invention; b) an antibody that binds said polypeptide, and c) a reagent for determining antigen-antibody binding.

Accordingly, in another aspect the present invention provides a kit comprising at least one oligonucleotide or polynucleotide primers capable of amplifying a polynucleotide which encodes a polypeptide of the invention, and optionally a polynucleotide which encodes a polypeptide of the invention, for use in detecting the presence of *Mycobacterium avium* subspecies *paratuberculosis*.

Accordingly, in another aspect the present invention provides a kit which is capable of detecting the presence of *Mycobacterium avium* subspecies *paratuberculosis* at a preclinical phase of Johne's disease.

Accordingly, in another aspect the present invention provides a cell-line, vector, or construct which includes a polynucleotide capable of encoding a polypeptide of the invention or functional variant or fragment thereof.

Accordingly, in another aspect the present invention provides a host cell incorporating a vector or construct of the invention capable of expressing a polypeptide of the invention or functional variant or fragment thereof Accordingly, in another aspect the present invention provides a host cell wherein said vector exists within the host cell as a plasmid.

Accordingly, in another aspect the present invention provides a host cell wherein said vector is integrated into the genome of the host cell.

Accordingly, in another aspect the present invention provides a method of transforming a cell with a polynucleotide capable of encoding a polypeptide of the invention or functionally equivalent variant or fragment thereof.

DESCRIPTION OF THE DRAWINGS

While the present invention is broadly as defined above, it also includes embodiments of which the following description provides examples. In particular, a better understanding of the present invention will be gained through reference to the accompanying drawings in which:

FIG. 1 depicts the amino acid sequence of the protein (SEQ ID NO. 1) as inferred from the nucleotide sequence partially obtained from clone pTB-16, and subsequently amplified from the genome of *M. ptb* ATCC 53950 and sequenced. The amino acids comprising the signal sequence are underlined.

FIG. 2 depicts the nucleotide sequence (SEQ ID NO. 2) of the 705 base pair gene that encodes the protein. The nucleic acids encoding the amino acids comprising the signal sequence are underlined.

FIG. 3 shows the expression of the recombinant his-tagged protein from *M. smegmatis*. Protein was prepared from sonicated cells harbouring plasmid pMIP-p22 or pMIP 12. Resulting soluble and insoluble fractions were electrophoresed in 15% SDS-PAGE gels. (a) Coomassie Blue stained gel. (b) Western blot analysis using 1:500 anti-histidine×6 POD conjugated antibody. Lane M, molecular weight standard; lane 1, pMIP12 insoluble; lane 2, pMIP12 soluble; lane 3, pMIP-p22 insoluble; lane 4, pMIP-p22 soluble. Lanes 5 to 8 contain protein fractions collected from $Ni^{+2}$-affinity chromatography of the soluble fraction of cells harbouring pMP-p22. Lane 5, unbound protein; lane 6, 40 mM imidazole elution; lane 7,250 mM imidazole elution; lane 8, 1 M imidazole elution. Recombinant histidine-tagged protein is indicated by the arrows.

FIG. 4 shows detection of antibody to the protein of the invention in sheep vaccinated with Neoparasec, such that of 11 sheep vaccinated with the live attenuated Neoparasec vaccine, 10 produced a strong antibody response to the protein. Western blots of recombinant protein were individually incubated with 1:1,000 dilution of sera Anti-sheep IgG POD conjugated antibody was used at 1:20,000. (a) Mob 1 sheep. Lane M, molecular weight standard (kDa); lanes 1 to 6, pooled three and seven month post-vaccination sera from animals 124, 127, 129, 131, 132 and 136, respectively. Lanes 7 to 12, pooled one and two month pre-vaccination sera from the same animals. Lane 13, anti-histidine×6 POD conjugated antibody control. (b) Mob 2 sheep. Lane M, molecular weight standard (kDa); lanes 1 to 5, post-vaccination sera from animals 507, 578, 587 (three month post-vaccination), 598* (two month post-vaccination), and 560* (one month post-vaccination), respectively. Lanes 6 to 10, one month pre-vaccination sera from the same animals, respectively. Lanes 11 to 14, sera from unvaccinated animals 599, 569, 527 and 538, respectively, taken at the equivalent of three months post-vaccination. * died after this time FIG. 5 shows the detection of antibody to the protein of the invention in individual sheep from a naturally infected flock. Western blots of recombinant protein were individually incubated with 1:500 dilution of serum. Anti-sheep IgG POD conjugated antibody was used at 1:40,000 dilution. Blots were developed by chemiluminescent detection. Lane M, molecular weight standard (kDa); lanes 1 to 14, sheep number 48, 44, 40, 36, 6, 13, 2, 23, 51, 32, 25, 27, 26 and 43, respectively. * animals diagnosed with Johne's disease.

FIG. 6 shows the detection of antibody to the protein of the invention in naturally infected cattle. Western blots of recombinant protein were individually incubated with 1:500 dilution of serum. Anti-bovine IgG POD conjugated antibody was used at 1:20,000 dilution. Blots were developed by chemiluminescent detection. Lanes M, molecular weight standard (kDa); lane 1 anti-histidine×6 POD conjugated antibody control; lanes 2 to 14, preclinical cattle which tested positive on at least one faecal culture (animal 242, 275, 144, 327, 181, 115, 34, 49, 517, 168, 58, 68, respectively); lanes 15 and 16, clinically affected (symptomatic) cattle (animal 27 and 25); lanes 17 to 22, cattle that were negative on all faecal culture and serum ELISA tests (animal 211, 132, 193, 97, 174, 53). The position of the protein of the invention is indicated on both sides by arrows. See Table 1 for ELISA and faecal culture results.

Figure 3:
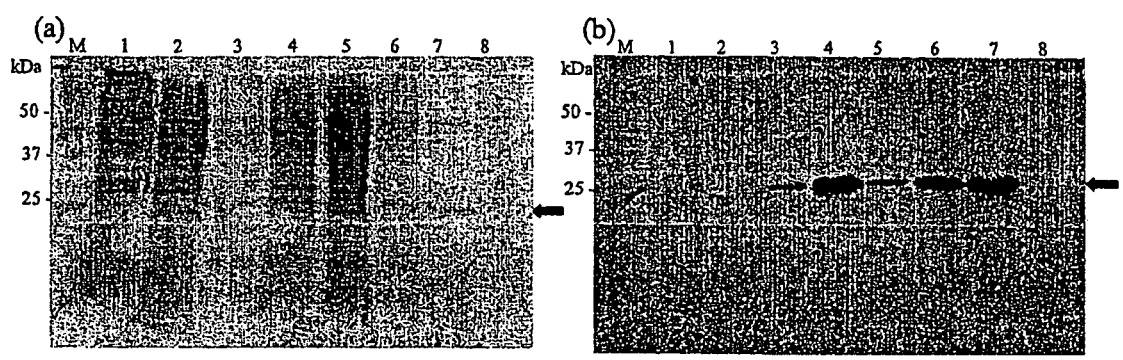
Figure 4:
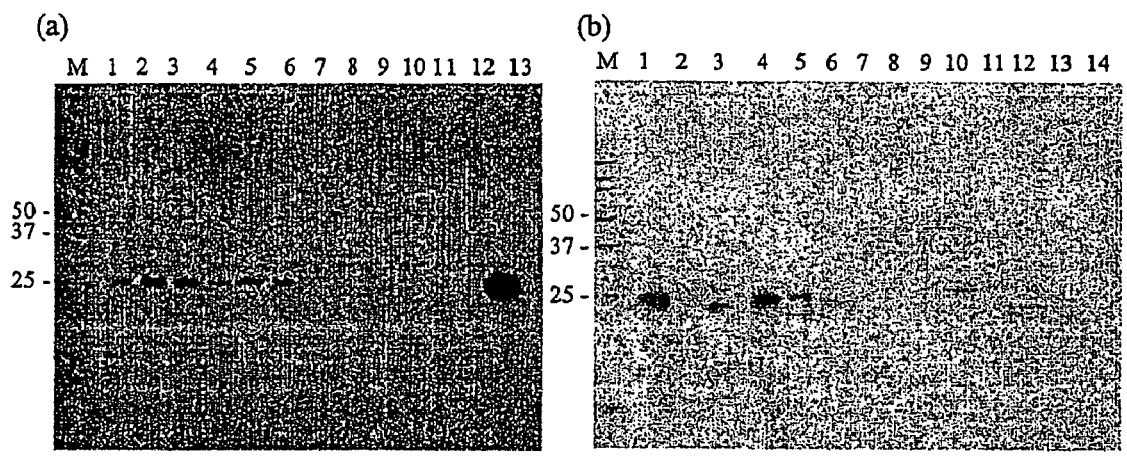

FIG. 12 shows PCR amplification of the gene encoding the protein of the invention from 13 isolates of *M. ptb*. PCR reactions were carried out using purified DNA as template and primer annealing at 62° C. Samples of 5 μl were electrophoresed in 1% agarose gels, stained with ethidium bromide and photographed under UV light Lane M, DNA size standard; lanes 1 to 3, New Zealand farmed deer isolates type C1; lanes 4 to 6, New Zealand sheep isolates type S1; lane 7, New Zealand sheep isolate type S5; lanes 8 and 9, South African sheep isolates type I; lane 10, New Zealand cattle isolate type C1; lane 11, Faeroe Islands sheep isolate type S2. The DNA from the five IS900-typed strains were gifted by Dr. Desmond Collins, AgResearch, Wallaceville Animal Research Centre, New Zealand. Lane 12, ATCC 53950; lane 13, strain 316F; lane 14, negative control (water).

FIG. 13 shows PCR amplification from 22 mycobacterial strains using primers designed to the ORF encoding the protein of the invention. PCR reactions were carried out using primers 1pp-27fBam and 1pp27-rKpn at two annealing temperatures. Samples of 5 μl were electrophoresed on 1% agarose gels, stained with ethidium bromide and photographed under UV light Simultaneous amplification of the 16S rRNA gene was carried out for each sample as a positive control (a single representative is shown). (a) 55° C. annealing temperature. (b) 62° C. annealing temperature. Lane M, DNA size standard; lane 1, *M. ptb* ATCC 53950; lane 2, *M. ptb* 316F; lane 3, *M. intracellularae*; lane 4, *M. scrofulaceum*; lane 5, *M. fortuitum*; lane 6, *M. tenrae*; lane 7, *M. phlei*; lane 8, *M. smegmatis*; lane 9, *M. kansasii*; lane 10, *M. gordonae*; lane 11, *M. marimum*; lane 12, *M. bovis* 35746: lane 13, *M. bovis* 19210; lane 14, *M. bovis* KML; lane 15, *M. bovis* 35725; lane 16, *M. bovis* 35726; lane 17, *M. bovis* canine isolate; lane 18, BCG (Pasteur); lane 19, BCG (Glaxo); lane 20, BCG (Japan); lane 21, *M. tuberculosis* $H_{37}$Ra; lane 22, *M. tuberculosis* fur seal isolate; lane 23, negative control (water); lane 24, representative positive control 16S rRNA from *M. ptb* ATCC 53950. The 725 base pair PCR product is indicated by the white arrow. The red arrow shows a weak 725 base pair product produced in the *M. tuberculosis* complex at 55° C.

FIG. 14 shows Southern blot analyses from genomic DNA of 13 mycobacterial strains using a probe to the gene encoding the protein of the invention. Approximately 1 μg of each DNA was digested with BamHI, electrophoresed and transferred to nylon membranes as described. Probe DNA was labeled by incorporation of DIG-dUTP during PCR of the ORF encoding the protein of the invention. The blot was developed with CDP-star and exposed to film for 2 h. Lane 1, *M. bovis* BCG (Pasteur); lane 2, *M. tuberculosis* $H_{37}$Ra; lane 3, *M. bovis* (KML); lane 4, *M. intracellularae*; lane 5, *M. ptb* 316F; lane 6, *M. scrofulaceum*; lane 7; *M. gordonae*; lane 8,

*M. konsasii*; lane 9, *M. phlei*; lane 10, *M. narinum*; lane 11, *M. terrae*; lane 12, *M. fortuitum*; lane 13, *M. ptb* ATCC 53950.

Figure 15:
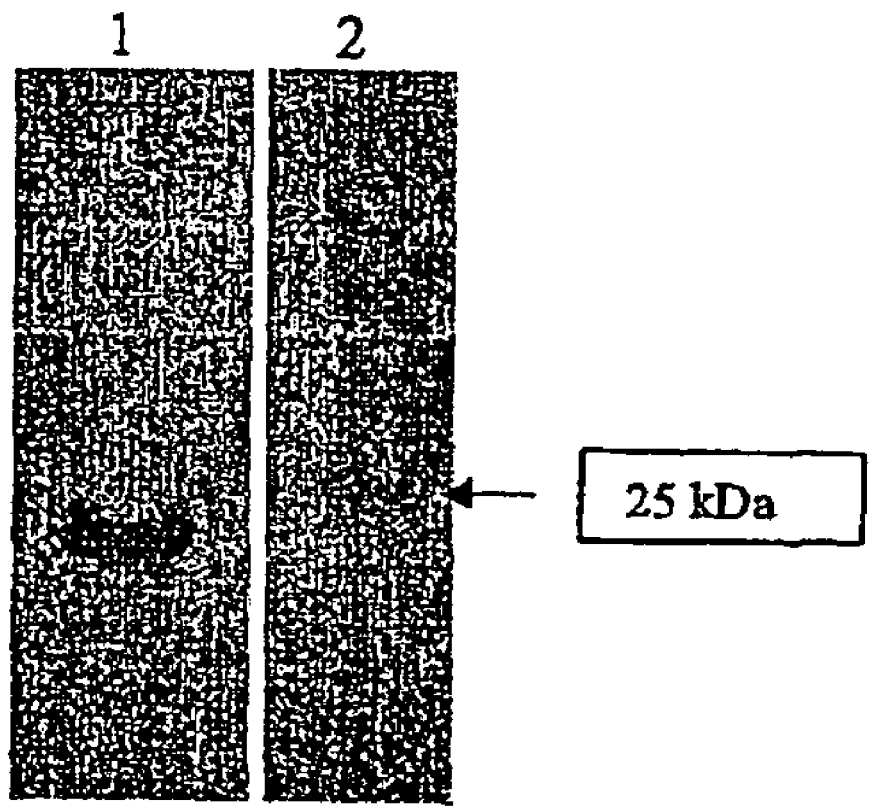

FIG. 15 depicts SDS-PAGE analysis showing (lane 1) concentrated protein of the invention from one of the batches used to prepare the recombinant protein of the invention vaccine used in this trial, and (lane 2) the molecular weights standard.

Figure 16:
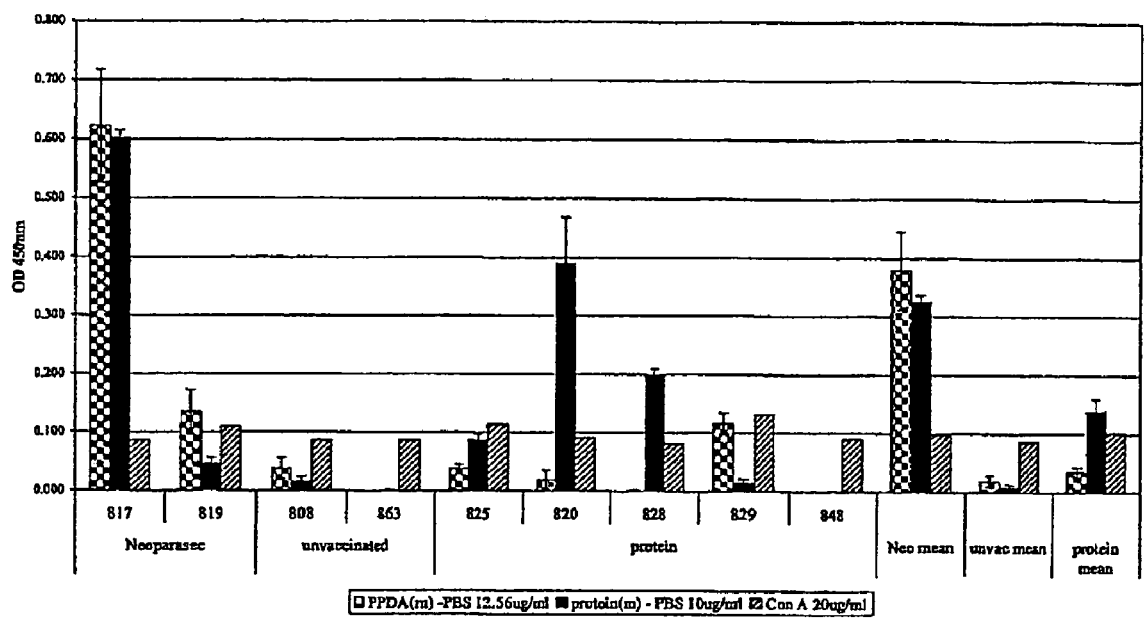

FIG. 16 depicts protein of the invention-elicited IFN-γ production in blood samples from the 5 sheep vaccinated with the protein of the invention, as compared with that from 2 of the Neoparasec vaccinated sheep, and two of the non-vaccinated sheep. The columns at the far right reflect the data means. Neo=Neoparasec vaccinated sheep, unvac=non-vaccinated sheep, and protein=protein of the invention-vaccinated sheep.

Figure 17:
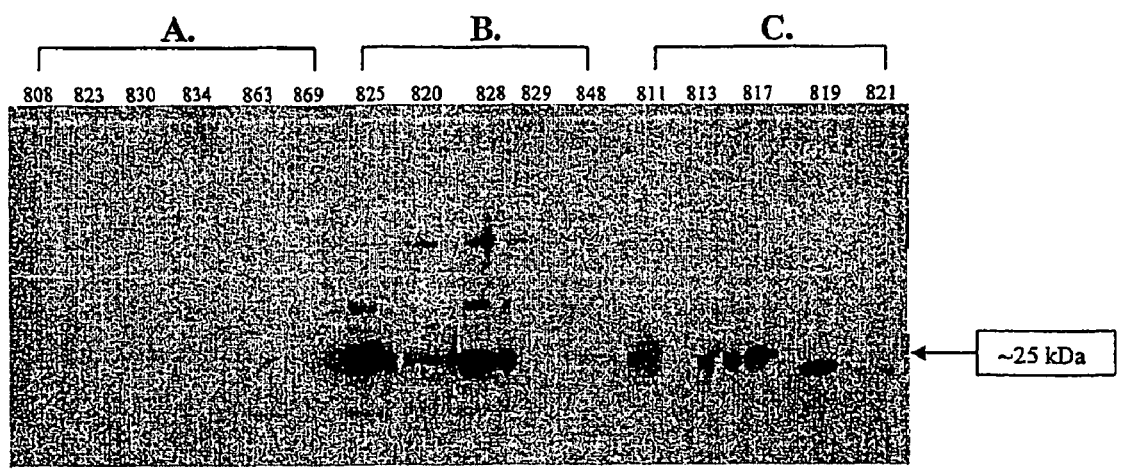

FIG. 17 shows a Western blot of recombinant protein of the invention, using for primary detection: A) serum from unvaccinated sheep; B) serum from sheep vaccinated with recombinant protein of the invention; C) serum from Neoparasec vaccinated sheep. The numbers represent the identification numbers of the individual sheep from which the serum was drawn.

Figure 18:
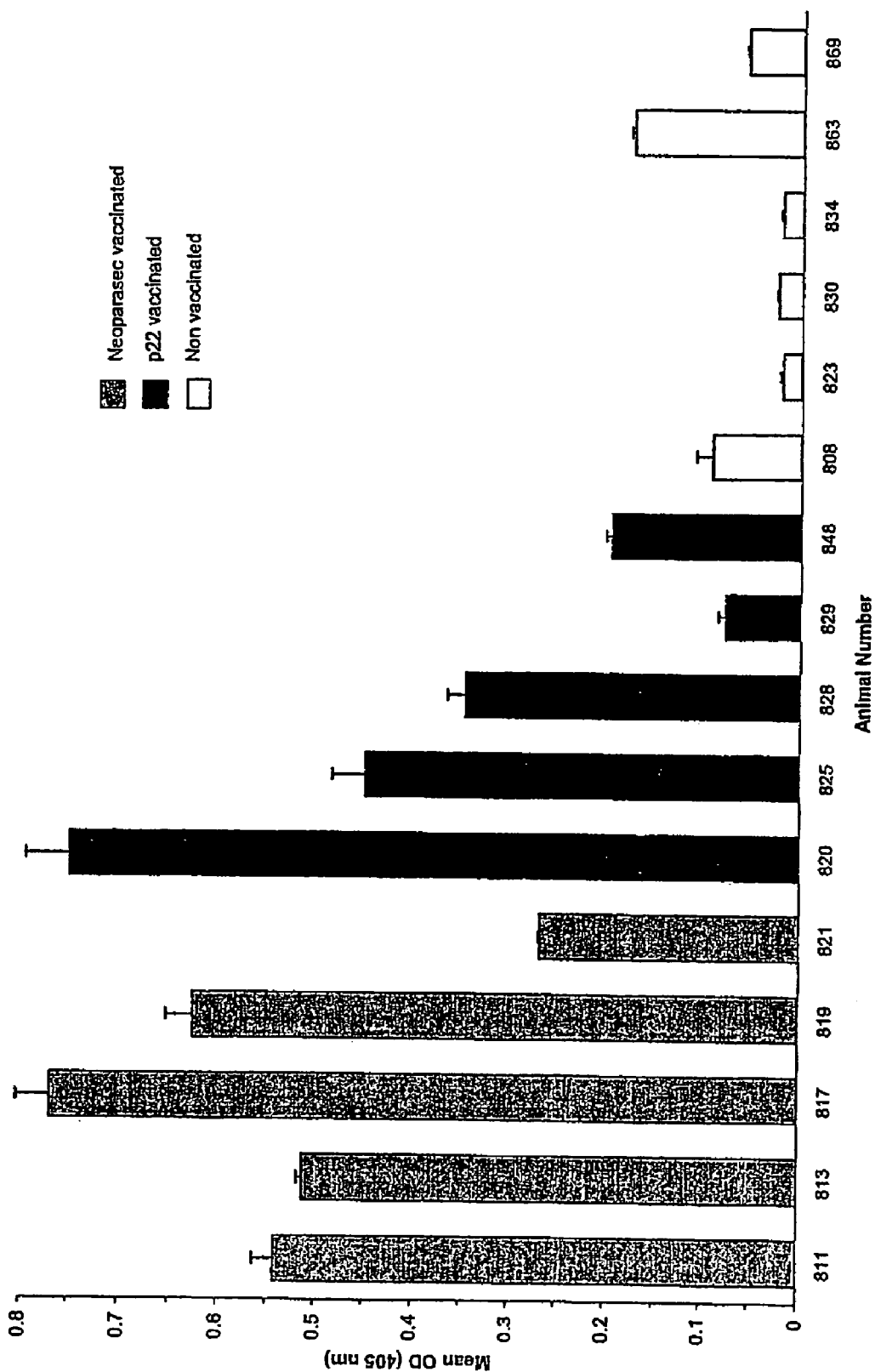

FIG. 18 shows detection of antibodies specific to the protein of the invention in serum (diluted 1:200) 5 weeks post vaccination.

Figure 19:
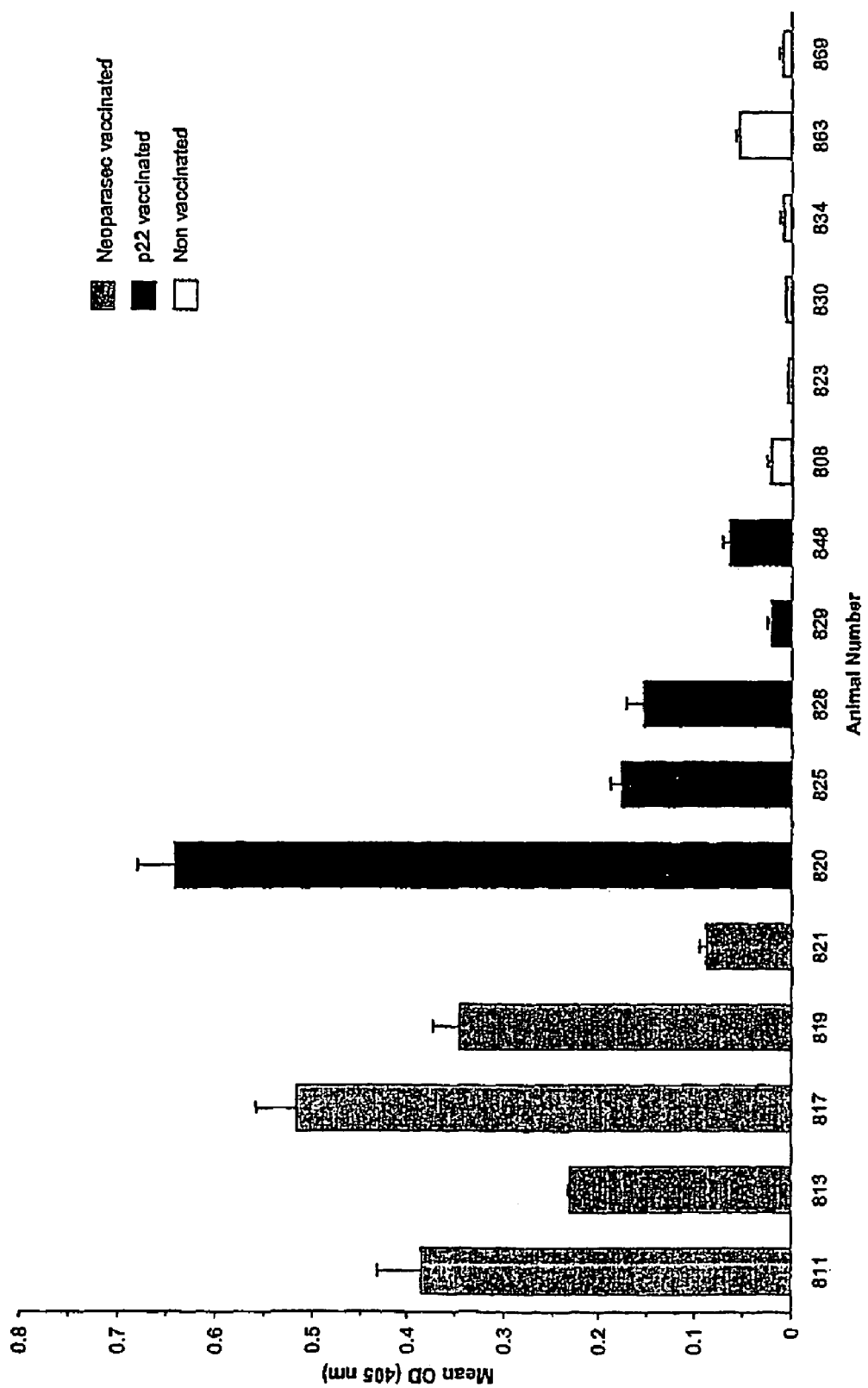

FIG. 19 shows detection of antibodies specific to the protein of the invention in serum (diluted 1:800) 5 weeks post vaccination.

DESCRIPTION OF THE INVENTION

As broadly outlined above, in one aspect the invention provides a novel protein which has the amino acid sequence as set forth in FIG. 1 (SEQ ID NO. 1).

The molecular weight of the protein is 22 kfDa, as assessed by SDS-PAGE. Amino acid sequence analysis suggests the protein is a lipoprotein. The protein can be detected in the culture filtrate of *M. ptb*, suggesting it is a weakly associated envelope protein.

The protein of the invention can include its entire native amino acid sequence or can include only parts of that sequence where such parts constitute fragments which remain biologically active (active fragments). Such activity will normally be as an immunogen, but is not restricted to this activity.

Analogs of the protein and of its encoding polynucleotides are also within the scope of the present invention. Such analogs include functionally equivalent variants of the protein and of the polynucleotides described below.

The invention also includes within its scope functionally equivalent variants of the protein of FIG. 1 (SEQ ID NO. 1).

The phrase "frictionally equivalent variants" recognises that it is possible to vary the amino acid sequence of a protein while retaining substantially equivalent functionality. For example, a protein can be considered a functional equivalent of another protein for a specific function if the equivalent peptide is immunologically cross-reactive with and has at least substantially the same function as the original protein.

The functionally equivalent protein need not be the same size as the original. The equivalent can be, for example, a fragment of the protein, a fusion of the protein with another protein or carrier, or a fusion of a fragment with additional amino acids. Active fragments may be obtained by deletion of one or more amino acid residues of full-length protein of the invention. It is also possible to substitute amino acids in a sequence with equivalent amino acids using conventional techniques. Groups of amino acids normally held to be equivalent are:

(a) Ala, Ser, Thr, Pro, Gly;
(b) Asn, Asp, Glu, Gln;
(c) His, Arg, Lys;
(d) Met, Leu, Ile, Val; and
(e) Phe, Tyr, Trp.

That equivalent may, for example, be a fragment of the protein containing from 8 to 50 amino acids, a substitution, addition or deletion mutant of the protein, or a fusion of the protein or a fragment or a mutant with other amino acids.

It is of course also possible (and expressly contemplated) that the bioactive peptides be or include any one of the octapeptides, nonapeptides, or decapeptides from the sequence.

Peptides which are, or include an octapeptide, nonapeptide or decapeptide from the protein of the invention from *M. ptb* ATCC 53950 are preferred.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); The Immunoassay Handbook (David Wild, ed., Stockton Press NY, 1994); Antibodies: A Laboratory Manual (Harlow et al., eds., 1987); and Methods of Immunological Analysis (R. Masseyeff, W. H. Albert, and N. A. Staines, eds., Weinheim: V C H Verlags gesellschaft mbH, 1993).

Polypeptide sequences may be aligned, and percentage of identical amino acids in a specified region may be determined against another sequence, using computer algorithms that are publicly available. The similarity of polypeptide sequences may be examined using the BLASTP algorithm BLASTP software is available on the NCBI anonymous FTP server. The use of the BLAST family of algorithms, including BLASTP, is described at NCBI's website and in the publication of Altschul, Stephen F., et al. (1997), "Gapped BLAST and PSI-BLAST: a new generation of protein database search programs", *Nucleic Acids Res.* 25:3389-34023.

Polypeptides of the invention also include homologous polypeptides having an amino acid sequence with at least 77% identity to the protein of the invention, preferably at least about 80% identity, more preferably at least about 90% identity, as well as those polypeptides having an amino acid sequence at least about 95%, 96%, 97%, 98%, and 99% identical to the protein.

Variants of the protein may be prepared using standard mutagenesis techniques such as oligonucleotide-directed site specific mutagenesis.

The invention also encompasses active fragments with bioactive functionality of the protein. Such active fragments may be obtained by deletion of one or more amino acid residues of full-length protein. Active fragments or portions of the protein may be ascertained by stepwise deletions of amino acid residues, from the N-terminal end or the C-terminal end or from within the polypeptide. If an amino acid is deleted and the bioactivity of the protein is not substantially reduced, then the amino acid may not comprise a portion of the active fragment. Further, polypeptides comprising an active fragment of the protein or its analog(s) are also encompassed in the invention.

A protein of the invention, its active fragments or other variants may be generated by synthetic or recombinant means (i.e. single or fusion polypeptides). Polypeptides, especially shorter polypeptides up to about 50 amino acids, are conveniently made by chemical synthesis using techniques well known to those of ordinary skill in the art. For example, to be prepared synthetically, the protein or its active fragments or other variants may be synthesised using any of the commercially available solid phase techniques such as the Merryfield solid phase synthesis method, where amino acids are sequentially added to a growing amino acid chain (see Merryfield, *J Am. Soc.* 85:2146-2149 (1963)). Equipment for automative synthesis of peptides is also commercially available from suppliers such as Perkin Elmer/Applied Biosystems, Inc and may be operated according to the manufacturers instructions.

The protein may also be produced recombinantly by inserting a polynucleotide (usually DNA) sequence that encodes the protein into an expression vector and expressing the peptide in an appropriate host. Any of a variety of expression vectors known to those of ordinary skill in the art may be employed. Expression may be achieved in any appropriate host cell that has been transformed or transfected with an expression vector containing a DNA molecule which encodes the recombinant peptides. Suitable host cells include prokaryotes, yeasts and higher eukaryotic cells. Preferably, the host cells employed are *Escherichia coli, Mycobacterium smegmatis*, yeasts or a mammalian cell line such as COS or CHO, or an insect cell line, such as SF9, using a baculovirus expression vector. The selection of suitable transcription and translation control elements, such as promoters, terminators, enhancers, ribosome-binding sites, termination signals and the like, for expression in the host cell is well known in the art. For example, in a preferred embodiment, the protein of the invention may be expressed in *E. coli* utilizing a high level expression system under the control of an inducible promoter, such as any of the pET (Novagen) vectors, which utilize the T7 promoter. The DNA sequence expressed in this matter may encode the naturally occurring protein, fragments of the naturally occurring protein or variants thereof.

DNA sequences encoding the protein or fragments may be obtained by screening an appropriate *M. ptb* cDNA or genomic DNA library for DNA sequences that hybridise to degenerate oligonucleotides derived from partial amino acid sequences of the protein. Suitable degenerate oligonucleotides may be designed and synthesised by standard techniques and the screen may be performed as described, for example, in Maniatis et al. Molecular Cloning—A Laboratory Manual, Cold Spring Harbour Laboratories, Cold Spring Harbour, NY (1989). The polymerase chain reaction (PCR) may be employed to isolate a nucleic acid probe from genomic DNA, a EDNA or genomic DNA library. The library screen may then be performed using the isolated probe.

Variants or homologues of the above polynucleotide sequences also form part of the present invention. Polynucleotide sequences may be aligned, and percentage of identical nucleotides in a specified region may be determined against another sequence, using computer algorithms that are publicly available. Two exemplary algorithms for aligning and identifying the similarity of polynucleotide sequences are the BLASTN and FASTA algorithms. The BLASTN software is available on the NCBI anonymous FTP server. The BLASTN algorithm version 2.0.4 [Feb. 24, 1998], set to the default parameters described in the documentation and distributed with the algorithm, is preferred for use in the determination of variants according to the present invention. The use of the BLAST family of algorithms, including BLASTN, is described at NCBI's website and in the publication of Altschul, Stephen F, et al (1997). "Gapped BLAST and PSI-BLAST: a new generation of protein database search programs", Nucleic Acids Res. 25:3389-3402. The computer algorithm FASTA is available on the Internet at the ftp site. Version 2.0u4, February 1996, set to the default parameters described in the documentation and distributed with the algorithm, is preferred for use in the determination of variants according to the present invention The use of the FASTA algorithm is described in the W R Pearson and D. J. Lipman, "Improved Tools for Biological Sequence Analysis," Proc. Natl. Acad. Sci. USA 85:2444-2448 (1988) and W. R. Pearson, "Rapid and Sensitive Sequence Comparison with FASTP and FASTA," Methods in Enzymology 183:63-98 (1990).

Vectors and/or cells lines which express the protein, a functionally equivalent variant or active fragment thereof, have utility in their own right and also form part of the invention.

The invention also includes isolated nucleic acid molecules or polynucleotides that comprise a polynucleotide sequence as set forth in FIG. 2 (SEQ ID NO. 2) encoding an ORF having at least about 77% identity, preferably 80% identity, preferably at least about 85% identity, more preferably at least about 90% identity, as well as those polynucleotides having a nucleic acid sequence at least about 95%, 96%, 97%, 98%, or 99%, identical to the protein polynucleotide sequence set forth in FIG. 2 (SEQ ID NO. 2).

Nucleic acid molecules of the invention may be in the form of RNA such as MnRNA or in the form of DNA, including cDNA, and genomic DNA obtained by cloning or produced synthetically. The DNA may be double stranded or single stranded. Single stranded DNA may be the coding (sense) strand or the non-coding (anti-sense) strand.

All sequences identified as above qualify as "variants" as that term is used herein.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. Such hybridizable sequences include those which code for the equivalent protein from sources (such as other *Mycobacterium*) other than *M. ptb.*

While the above synthetic or recombinant approaches can be taken to produce the protein of the invention, it is however practicable to obtain the protein by isolation from *M. avium* and/or a subspecies or strain thereof, or a culture filtrate from *M. avium*, and/or a subspecies or strain thereof.

Particularly suitable subspecies of *M. avium* from which the protein can be isolated are *M. ptb*, with *M. ptb* strain ATCC 53950 being presently preferred.

Once obtained, the protein is readily purified if desired. This may involve affinity chromatography in which the immunogenic nature of the protein is important.

Other approaches to purification (eg. gel-filtration or anion exchange chromatography) can however also be followed. Where the protein or fragment is produced in the form of a fusion protein, the carrier portion of the fusion protein can prove useful in this regard.

Furthermore, if viewed as desirable, additional purification steps can be employed using approaches which are standard in this art. These approaches are fully able to deliver a highly pure preparation of the protein. Preferably, the protein preparation comprises at least about 50% by weight of the protein, preferably at least about 80%, preferably at least about 90%, and more preferably at least about 95% by weight of the protein.

The purification procedure will of course depend on the degree of purity required for the use to which the protein or fragment is to be put.

Once obtained, the protein and/or its active fragments and/or its functionally equivalent variants can be formulated into a composition The composition can be, for example, a therapeutic composition for application as a veterinary pharmaceutical, a vaccine, or a diagnostic composition. For these purposes it is generally preferred that the protein be present in a pure or substantially pure form.

Again, standard approaches can be taken in formulating such compositions (see for example, Remington's Pharmaceutical Sciences, 18th Edition, Mack Publishing (1990)).

In one embodiment, the protein, its functionally equivalent variants or active fragments are employed as antigens to elicit a host-protective response in an animal. It will be appreciated that in accordance with this embodiment, the antigen of the invention can be administered either alone or in the form of a composition including a vaccine preparation comprising the antigen as the active ingredient together with a pharmaceutically acceptable diluent, carrier, excipient, or adjuvant.

Examples of suitable adjuvants known to those skilled in the art are saponins (or derivative or related material), muramyl dipeptide, trebalose dimycollate, Freund's complete adjuvant, Freund's incomplete adjuvant, other water-in-oil emulsions, double emulsions, dextran, diethylaminoethyl-dextran, potassium alum, aluminium phosphate, aluminium hydroxide, bentonite, zmosan, polyelectrolytes, retinal, calcium phosphate, protamine, sarcosine, glycerol, sorbitol, propylene glycol, fixed oils and synthetic esters of higher fatty acids. Saponins are generally preferred.

The antigen of the invention may also be treated in any conventional way to enhance its stability or to conserve or potentiate its immunogenic efficacy. For example, the antigen may be treated with a suitable inhibitor, modifier, crosslinker, or denaturant in such a way as to enhance its immunogenicity.

In addition, the antigen can be administered in combination with other therapeutic agents.

It is also possible to include an additional immunogen in the solution or composition for administration as a vaccine. Such an immunogen will generally be a Th1 type immune response inducing substance.

An immunogenic composition including a vaccine of the invention can be administered to the animal by any of those methods known in the art. However, the preferred mode of administration is parenteral. The term "parenteral" is used herein to mean intravenous, intramuscular, intradermal, and subcutaneous injection. Most conveniently, the administration is by subcutaneous injection.

Despite the preference for parenteral administration, it is by no means intended to exclude administration of the immunogenic composition in other forms.

Administration of the immunogenic composition of the invention may be conveniently carried out at a single time point. Alternatively, the immunogenic composition may be administered more than once.

The amount of composition administered to the animal to be treated will depend on the type, size and body weight of the animal as well as on the immunogenicity of the immunogenic composition. Conveniently, in the case of a vaccine, the vaccine is formulated such that relatively small volumes of vaccine (1 to 5 mL) are sufficient to protect the animal to which they are administered. Similarly, where the immunogen of the vaccine is the protein of the invention or a functional variant or fragment thereof as described herein, the vaccine may be formulated so that a dose comprises between 0.1 µg and 1000 µg immunogen per kg body weight of animal, more preferably between 5 µg and 500 µg per kg, more preferably between 10 µg and 100 µg per kg.

The term "animal" as used herein includes ruminants such as cattle, sheep, deer, buffalo, camelids, antelope, and goats. Sheep are particularly suitable for use with the invention In addition to the vaccine embodiments described above, it will be understood that a live vaccine could also be employed to protect a host against *M. ptb* infection or Johne's disease. In such a live vaccine, the DNA molecule of the invention encoding the protein, functionally equivalent variant or active fragment thereof, is incorporated into the genome of an attenuated carrier organism. A number of carrier organisms are known in the art which are suitable for this purpose with examples being *Salmonella* and *Vaccinia* virus.

The live vaccine of this embodiment can be formulated in accordance with methods known in the art. Similarly, the live vaccine can be administered parenterally, or by conventional methods to have its effect via the gastrointestinal tract.

It is well known by those skilled in the art that *M. ptb* is the causative pathogen of Johne's disease. A further use of the protein of the invention, its functionally equivalent variant or active fragment thereof, is in the field of diagnosis of *M. ptb* infection and/or Johne's disease. More particularly, it will be understood by those persons skilled in the art that the protein, functionally equivalent variant or active fragment thereof, may be employed as highly specific diagnostic reagents for detection of the presence of *M. ptb* in an animal suspected of harbouring the disease. The diagnostic procedure employed to detect *M. ptb* and/or Johne's disease may involve the detection of delayed type hypersensitivity to the protein of the invention by skin test or the like, or may involve an assay of body fluid obtained from the animal.

Similarly, the diagnostic procedure employed to detect *M. ptb* and/or Johne's disease may involve the use of the protein of the invention as a reagent in an IFN-γ EIA test.

It will be understood by those persons skilled in the art that the detection system selected may employ the protein, functionally equivalent variant or active fragment thereof, alone as diagnostic reagents.

However, in other systems such diagnostic reagents will include suitable carrier or marker substances (either chemical, enzymic or radiochemical) in the detection of antibodies by agglutination, radioimmunoassay, fluorescence or enzyme immunoassay techniques. A preferred antibody detection technique is ELISA.

Another use for the polypeptides of the invention is the generation of antibodies, including monoclonal antibodies. Polypeptides of the invention are used as immunogens to immunize mice. Splenocytes (including lymphocytes) are obtained from the immunized mice. Hybridomas are prepared from the lymphocytes and immortalized myeloma cells using the general somatic cell hybridization technique of Kohler, B. and Milstein, C. Nature 256:495-497 (1975). Other modified methods, for example by Buck, D. W., et al., In Vitro, 18:377-381 (1982) may also be used. Available myeloma lines, including but not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein, supplemented with or without serum, can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants ale assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbants made of the immunogen attached to a solid phase and eluting or releasing the desired antibodies off the immunogen.

Polypeptides of the invention may also be used as immunogens to immunize other animals (i.e., rats and rabbits) to generate polyclonal antibodies. Methods of producing polygonal antibodies and isolation and purification thereof is known in the art. See, for example, Harlow and Lane (1987). Other suitable techniques for preparing antibodies involve in vitro exposure of lymphocytes to the antigen or alternatively to selection of libraries of antibodies in phage or similar vectors. See, for example Huse et al., 1989.

Also, recombinant antibodies may be produced using procedures known in the art. See, for example, U.S. Pat. No. 4,816,567.

The antibodies may be used with or without modification. Frequently, antibodies will be labeled by joining, either covalently or non-covalently a substance which provides a detectable signal. A wide variety of labels and conjugation techniques are known and are reported extensively in the literature.

Antibodies as above to the protein of the invention can therefore be used to detect or monitor the presence of the protein in an animal or in protein quantification assays. Further, antibodies to the protein of the invention can be used to measure levels of the protein in an animal, either at one fixed time point or over a period of time to monitor fluctuations in protein levels. Such antibodies can also be used to measure levels of the protein in an animal to which drugs, vaccines, or other therapeutic or prophylactic bioactives have been administered. In such assays, any convenient immunological format can be employed. Such formats include immunohistochemical assays, RIA, IRMA and ELISA assays.

The assays can be conducted in relation to any biological fluid which does, or should, contain the protein of the invention. Such fluids include blood, serum, plasma, urine and cerebrospinal fluid.

Antibodies as above to the protein of the invention can therefore be used to detect or monitor the presence of *M. ptb* and/or Johne's disease in an animal or in *M. ptb* quantification assays. Further, such antibodies can be used to measure levels of *M. ptb* in an animal, either at one fixed time point or over a period of time to monitor fluctuations in *M. ptb* levels. Such antibodies can also be used to measure levels of *M. ptb* in an animal to which drugs, vaccines, or other therapeutic or prophylactic bioactives have been administered. In such assays, any convenient immunological format can be employed. Such formats include immunohistochemical assays, RIA, IRMA and ELISA assays.

The assays can be conducted in relation to any biological fluid which does, or should, contain the protein of the invention, a functionally equivalent variant or active fragment thereof, and/or *M. ptb*. Such fluids include blood, serum, plasma, urine and cerebrospinal fluid.

Antibodies, monoclonal or polyclonal, against the protein of the invention may be used for diagnosis or for therapeutic purposes. Antibodies may be used by themselves or attached to a solid substrate, such a column or a plate. Antibodies which are attached to a solid substrate may be used for assays, for example ELISA, or as a standard in other assays. Antibodies against the protein of the invention are also useful for isolation, purification, and quantitation of the protein of the invention.

Those skilled in the art will appreciate that the functional equivalents of antibodies, such as antibody fragments and/or $f_{ab}$ molecules are also considered herein.

The antibodies can also be included in assay kits. Such kits can contain, in addition, a number of optional but conventional components, the selection of which will be routine to the art skilled worker. Such additional components will however generally include a protein reference standard, which may be the protein of the invention itself or an analog.(such as a fragment).

It will also be appreciated that antibodies such as described above can, in some circumstances also function as antagonists of the protein of the invention by binding to the protein and partly or completely interfering with its activity.

Similarly, those skilled in the art will appreciate that other ligands that bind the protein of the invention, a functionally equivalent variant or active fragment thereof, may be used in a fashion analogous to the antibodies to the protein described above.

Aspects of the invention will now be described with reference to the following non-limiting examples.

EXAMPLE 1

To identify potential exported proteins of *M. ptb*, a library of alkaline phosphatase (phoA) gene fusions was constructed in the vector pJEM11 and expressed in *Escherichia coli* and *Mycobacterium smegmatis*.

Materials and Methods

Extraction of DNA from *M. ptb*

Approximately 3 mg of lyophilized *M. ptb* (New Zealand field isolate ATCC 53950) was resuspended in 0.6 ml of extraction buffer (100 mM NaCl, 25 mM EDTA (pH 8.0), 10 mM Tris.Cl pH 8.0, 0.5%(w/v) SDS) before adding 200 μg of proteinase K (Roche Molecular Biochemicals, Germany). The mixture was incubated at 50° C. for 18 h and then 100 μl of 5 M NaCl and 120 μl of 6.7% (w/v) cetyltrimethylammonium bromide (Aldrich Chemical Company, USA) in 0.5% (w/v) NaCl was added. The digest was mixed with an equal volume of 25:24:1 phenol:chloroform:isoamyl alcohol and centrifuged at 15,800×g for 5 min. The aqueous phase was collected and the phenol:chloroform:isoamyl alcohol extraction was repeated, as above. The aqueous phase was mixed with an equal volume of chloroform and centrifuged again. The DNA was precipitated with the addition of 1 volume of 100% isopropanol to the collected aqueous phase. After 18 h at −20° C., the DNA was pelleted by centrifugation at 15,800×g for 30 min at 4° C. The pellet was washed with 1 ml of 70% ethanol, air dried at room temperature and resuspended in 100 µl of TE buffer containing 100 µg/ml RNAse A (Life Technologies Inc., USA) and incubated for 18 h at 37° C. The DNA concentration was calculated based on absorbance at 260 nm. To check the condition of the DNA, an 8 µl sample (~11 µg) was electrophoresed on a 0.7% agarose gel, stained with ethidium bromide and visualised under WV light.

Preparation of pJEM11 Vector DNA pJEM11 plasmid DNA was purified from transformed *E. coli* DH10B cells. The plasmid DNA was quantitated based on its absorbance at 260 nm. Eleven micrograms of plasmid was digested to completion with 2.5 units of BamHI at 37° C. for 2 h and was purified by agarose gel extraction. The resulting digested plasmid DNA was dephosphorylated using 2 units of alkaline phosphatase (Boehringer Mannheim, Germany) for 1 h at 37° C. to prevent recircularization of the plasmid. The DNA was then purified by agarose gel extraction.

Partial Digestion of *M. ptb* Genomic DNA

A partial digest of *M. ptb* genomic DNA was performed on 2.8 µg of the DNA using 0.05 units Sau3A in a volume of 25 µl at 22° C. From this, 6×4 µl samples were removed at 30 s intervals and were electrophoresed on a 1% agarose gel. DNA ranging in size from approximately 200-3,000 base pairs was extracted from the 1.5 min and 2.0 min digestion lanes from the agarose gel. The resulting DNA fragments were eluted in a final volume of 50 µl of TE buffer. A 10 µl sample was run on a 1% agarose gel to check recovery.

Ligation of Size Selected *M. ptb* Genomic DNA and PJEM11 and Transformation into *E. coli*

Approximately 1 µg of BamHI, alkaline phosphatase-treated pJEM11 vector DNA and 0.7 µg of Sau 3A partially digested *M. ptb* DNA were ligated using 1.0 unit of T4 DNA ligase in a total volume of 35 µl at room temperature for 30 min. The mixture was dialysed and electroporated into 100 µl of *E. coli* DH10B cells. To this, 500 µl of LB broth was added and incubated for 1 h at 37° C. Aliquots of approximately 70 µl each were plated onto nine LB/kan/BCIP plates and incubated at 37° C. for approximately 18 h. A representative plate was selected and colonies were counted on a quarter of the plate to estimate the total number of resulting transformants. The total number of blue transformants was also counted. Blue *E. coli* colonies were restreaked onto LB/kan/BCIP plates for confirmation of PhoA$^+$ phenotype. Each of these colonies was cultured in LB/kan broth for glycerol storage at −70° C.

Plasmid Isolation from the *E. coli* Recombinant Library

The recombinant plasmid library was then isolated from *E. coli*. To each of the nine plates, 1.6 ml of LB/kan broth was added and the colonies were resuspended with the aid of a rubber spatula The mixtures from each plate were transferred to 2 ml microtubes and the plasmid DNA was extracted using a BRESAspin Plasmid Mini Kit (Bresatec, Australia) with the modification that all reagent volumes were doubled due to the high concentration of cells. Each of the nine plasmid preparations was eluted into 50 µl of TE buffer, for a total volume of 450 µl. The plasmids were stored at −20° C. until used.

Transformation of the Recombinant Plasmids Into *M. smegmatis*

The recombinant plasmids were then transformed into *Mycobacterium smegmatis* mc$^2$155. Two 10 µl aliquots of the plasmid mixture were dialysed and used to transform two 100 µl aliquots of electrocompetent *M. smegmatis* cells. To each of the resulting transformations, 500 µl of LB broth was added and the cells were incubated at 37° C. for 2 h. From this, 80 µl samples were spread onto 15 LB/kan/BCIP plates, which were then incubated at 37° C. After five days, the plates were transferred to 4° C. for a farther 54 days. To estimate the total number of colonies (blue and white), a quadrant of a representative plate was counted. Over the 59 days, blue colonies were picked daily and designated numerically, as they appeared. These were restreaked onto fresh LB/kan/BCIP plates and grown at 37° C. until they turned blue and then were transferred to glycerol for storage at −70° C.

Sequencing of DNA Inserts Encoding Putative Exported Proteins

To obtain plasmid DNA for sequencing of inserts, the pJEM11 constructs were first transferred from individual *M. smegmatis* colonies to *E. coli* DH10B cells. Prior to sequencing, the clones were first screened for presence of unique inserts by digestion of the plasmids with restriction endonucleases Kpn I and Apa I, which flank the DNA inserts in pJEM11. Unique inserts were then selected for sequencing.

Results

Construction of an *M. ptb* pJEM11 Expression Library

In order to identify *M. ptb* gene sequences encoding exported proteins, a library of *M. ptb* phoA fusions was created in the vector pJEM11 as described above and expressed in *E. coil* and *M. smegmatis*.

Since *M. smegmatis* mc$^2$ 155 has a $10^4$ lower rate of transformation efficiency as compared to *E. coli* (Snapper et al. 1990), the plasmid library was first transformed into *E. coli* to ensure the highest possible proportion of constructs could be recovered.

After 18 h at 37° C. a representative *E. coli* plate had 1,200 colonies. This resulted in an estimated total of 10,800 colonies from nine plates. Of these, 17 colonies were blue. These were designated Eco-1 to Eco-17. Upon a further 18 h storage of the library at 4° C., seven more blue *E. coli* colonies resulted. These were designated Eco-18 to Eco-24. Thus, a total of 24 blue *E. coli* colonies, representing 0.2% of the library were obtained.

Expression of the Library in *M. smegmatis*

A sample of the plasmid collection was used to transform *M. smegmatis*. After three days incubation at 37° C. on LB/kan/BCIP plates, the first blue *M. smegmatis* colony appeared and was designated pTB-1. Over the next two days, a further 45 blue colonies appeared, designated pTB-2 to pTB46. The plates were transferred to 4° C. and 473 more blue colonies appeared over 54 days. A total of 519 blue *M. smegmatis* clones were collected. The total number of *M. smegmatis* colonies was estimated to be 60,000, of which 0.9% were blue.

A six-fold increase in the number of colonies was obtained in *M. smegmatis* (60,000) compared to *E. coli* (10,800). This was a result of amplification of the plasmids in *E. coli* prior to transfer to *M. smegmatis*. Multiple copies of the plasmids were therefore expected to be present in the *M. smegmatis* library. This expectation was confirmed by analysis of the pJEM11 plasmid constructs. The average insert size was calculated from PhoA$^+$ constructs analysed by agarose gel electrophoresis. The plasmids were digested with Apa I and Kpn I, whose recognition sites flank the Bam HI site in the vector used for cloning. Only unique inserts were included in calculations. From the 128 plasmids analysed, the average insert size was 1,700 base pairs. The inserts generally ranged in size from 300-3,000 base pairs with a median of 1,400 base pairs.

Insert DNA was fully or partially sequenced from 63 individual clones. Of these, 33 were unique in sequence and the rest were redundant. The partial gene sequences adjacent to phoA were used to search DNA and protein databases. Twenty-five of the 33 sequences obtained had similarities to other mycobacteria or *Streptomyces* genes and included identities with a copper/zinc superoxide dismutase, a cutinase, a penicillin-binding protein, a serine/threonine protein kinase and three lipoproteins. One sequence was identical to the previously characterised gene encoding the *M. ptb* 34 kDa protein. Seven sequences had no significant similarities to any of the sequences on the databases.

N-terminal regions were determined for 21 of the 33 translated open reading frames fused to phoA. These sequences were further analysed for the presence of conserved signal peptide elements and transmembrane-spanning regions. Twelve had evidence of signal sequences and four had predicted transmembrane segments. The remaining five had no evidence of characteristic hydrophobic stretches of amino acids that might function as transmembrane segments. Of the twelve sequences with indefinable N-termini, eight had predicted transmembrane-spanning regions.

A putative lipoprotein identified in this study was selected for further investigations.

EXAMPLE 2

An exported 23 kDa protein, identified as described above, was characterised and assessed for its immunoreactivity. The open reading frame encoding the protein was cloned and the protein was expressed in *M. smegmatis* as a C-terminal polylistidine-tagged recombinant protein as described below.

Materials and Methods

PCR Amplification of the Gene from *M. ptb*

Genomic DNA extracted from *M. ptb* ATCC 53950, prepared as described above, was used as a template for PCR amplification of the gene encoding the protein of the invention. Oligonucleotide primers were designed to the 5' and 3' ends of the entire ORF and are shown below. The forward primer 1pp27-fBam (SEQ ID NO. 3) was designed to the 5' end of the predicted ORF, and the reverse primer 1pp27-rKpn (SEQ ID NO. 4) was designed to the 3' end of the ORF. The TGA stop codon was omitted to allow read-through to produce the histidinex6 tag coded by the vector.

```
1pp27-fBam    5' GATGGGATCCATGCAGACCCGCCGCCGCCT

1pp27-rKpn    5' TGAGGGTACCCGAGCTCACCGGGGGCTTGG
```

PCR was done using 1 µl of a 1:10 dilution of genomic DNA template in a volume of 50 µl. The conditions used were an initial melting temperature of 95° C. for 10 min followed by 35 cycles of 94° C. for 30 s, 55° C. for 30 s, 68° C. for 1 min, and a final extension at 68° C. for 10 min using platinum Pfx polymerase, in the presence of 10%(v/v) dimethlysulfoxide.

Cloning of the Open Reading Frame

For expression of the gene encoding the protein of the invention in *M. smegmatis*, the ORF was cloned into the vector pMIP12. The 725 base pair PCR product was extracted from a 1% TAE agarose gel. The purified product was eluted in 30 µl of distilled water and a 6 µl sample was run on a 1% agarose gel to check its recovery. The remaining DNA was digested with 40 units of KpnI in 40 µl at 37° C. overnight. This was followed by digestion with BamHI in a total volume of 50 µl at 37° C. overnight. The digested product was purified and resuspended in 30 µl of sterile water using a QIAgen gel extraction kit. From this, 6 µl was electrophoresed on a 1% TAE agarose gel to estimate its concentration. The remainder was used for ligation with pHIP12, as described below.

The vector pMIP12 was isolated from previously transformed *E. coli* DH10B cells. Plasmid DNA from two 4 mn cultures grown in LB/kan broth was resuspended in 100 µl of distilled water. DNA concentration was quantitated by absorbance at 260 nm. Approximately 2.6 kg of plasmid DNA was digested with 20 units of KpnI in 20 µl for 4 h at 37° C. To confirm completion of digestion, 1 µl was removed and electrophoresed on a 1% TAE agarose gel and photographed. To the remaining 19 µl, 30 units of BamHI was added and the volume was brought up to 30 µl with water. The mixture was incubated for 18 h at 37° C. The digested vector was electrophoresed on a 1% low melting point agarose gel (SeaPlaque GTG agarose, FMC BioProducts, Rockland, Me., USA) in TAE buffer and ethidium bromide stained for visualisation. The gel slices were cut out in a minimal amount of agarose, transferred to a 1.5 ml microfuge tube and melted at 68° C. for 10 min. From this mixture, 6 µl was removed and immediately added to a microfuge tube containing 24 µl of insert DNA, prepared as described above. To this was added unit of T4 DNA ligase in a total volume of 40, and the mixture was incubated at 14° C. overnight. This was dialysed and electroporated into 35 µl of *E. coli* ElecrtoMax DH10B cells. To this, 200 µl of LB broth was added and the mixture was incubated at 37° C. for 1 h. Of this, 50 µl was spread onto a LB/kan plate and incubated overnight at 37° C.

To confirm the presence of the insert, PCR was carried out on five of the resulting colonies using the pMIP12 primers BlaF3 and R2 (see below), in the presence of Taq polymerase in 20 µl Eight microlitres from each PCR was electrophoresed on a 1% TAE agarose gel and ethidium bromide stained. The forward primer BlaF3 binds at approximately 150 base pairs within the blaF* promoter and is designed to the coding strand. The reverse primer R2 binds 44 base pairs from the KpnI site and is designed to the complementary strand of the transcriptional terminator. The expected size of the PCR product for the insert was approximately 900 base pairs.

```
BlaF3    5' TCGCGGGACTACGGTGCC       (SEQ ID NO: 5)

R2       5' TCGAACTCGCCCGATCCC.      (SEQ ID NO: 6)
```

From a resulting PCR-positive colony, plasmid DNA was extracted from 4 ml of broth culture and resuspended in 50 µl of 10 mM Tris (pH 8.0). Eight microlitres of plasmid was digested with 10 units of KpnI in 10 µl at 37° C. overnight. This was followed by digestion with 10 units of Bam HI in a final volume of 25 µl at 37° C. overnight. One microliters was electrophoresed on a 1% TAE gel and photographed after ethidium bromide staining. To confirm the insert identity and the correct insertion for expression, plasmid was used as template for sequencing using the primers Bla3 and R2.

Expression and Purification of Recombinant Protein from *M. smegmatis*

For transfer of pMIP-p22 into *M. smegmatis*, 1 µl of the plasmid DNA was electroporated into 20 µl of *M. smegmatis* cells. A 250 µl aliquot of cells was spread on a LBAcan plate and incubated at 37° C. for three days. To confirm the presence of pMP-p22, one colony was picked for PCR analysis using the primers R2 and Bla3 as described above, in a volume of 100 µl. The resulting 900 base pair product was gel-extracted and sequenced using the same primers.

For preparation of recombinant protein, a single colony of pMEP-p22-transformed *M. smegmatis* was picked and inoculated into 15 ml of Sauton's broth or modified Middlebrook 7H9 broth containing kan and grown at 37° C. with vigorous shaking for approximately three days. This was used to inoculate 600 ml of the same media, and the culture was grown and harvested and lysates were prepared as described.

The resulting sonicate supernatant was used in $Ni^{+2}$-affinity chromatography, employing four 5 ml columns connected in series and attached to a peristaltic pump. Imidazole concentrations of 40 mM, 250 mM and 1 M were used, in the first instance, to determine the elution profile of the recombinant protein. Samples from each collected elution were used in Western blot analyses to determine where the majority of the recombinant protein eluted. Having determined this, the procedure was repeated using two washes of 100 mM of imidazole prior to the 250 mM elution, to further purify the recombinant protein. Pooled fractions were concentrated as described, in preparation for Western blotting, IFN-γ assays or size exclusion chromatography.

N-terminal Protein Sequencing

Automated Edman degradative N-terminal sequencing was carried out by Massey University Protein Sequencing Services using a pulse liquid phase sequenator (Model 476A, Applied Biosystems, USA). This instrument performs fully automated sequencing by sequential removal of the N-terminal amino acid as a phenylthiohydantoin-derivative. Derivatives were separated by HPLC and the data collected and analysed using a Model 610A Data Analysis Module (Applied Biosystems, USA). Protein to be sequenced was electrophoresed on 15% SDS-PAGE gels and transferred to PVDF membrane as described. Following transfer, the membrane was stained with Ponceau S and the desired band(s) were excised and destained in distilled water. Approximately 1 pmol (25 μg for a protein of 25 kDa) of protein was used for sequencing.

Results

Expression and Purification of Recombinant Protein from *M. smegmatis*

Figure 5:
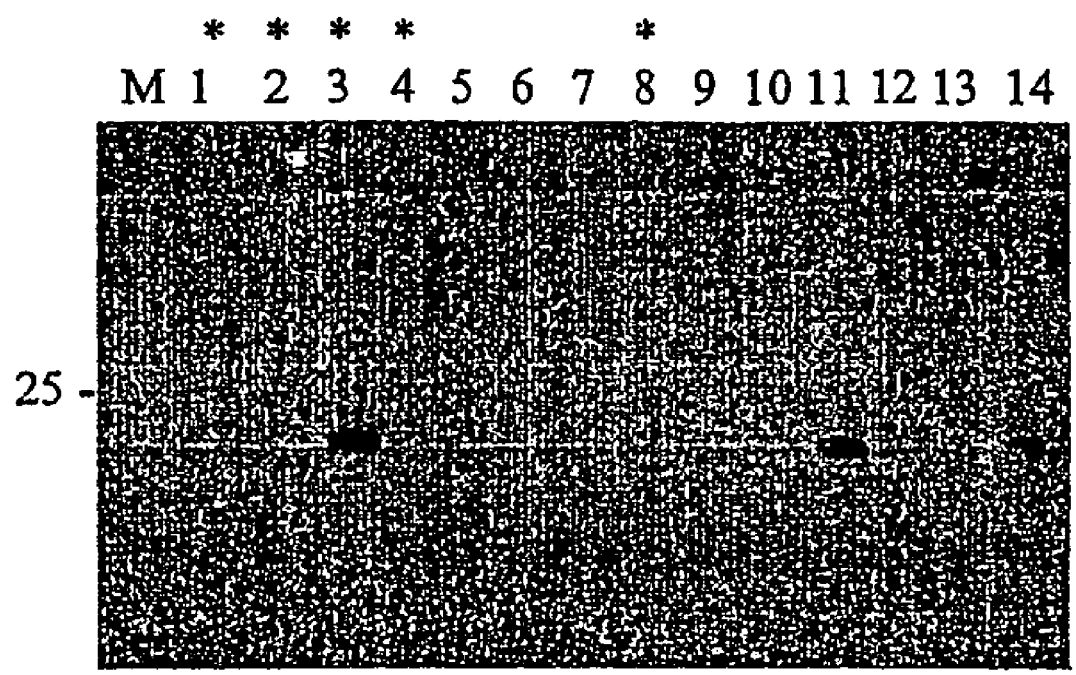

In order to increase the likelihood of producing the protein of the invention in a form resembling that from the original host (*M. ptb*), it was expressed in the fast-growing species *M. smegmatis*. The ORF encoding the protein of the invention was cloned into the vector pMIP12 and used to transform *M. smegmatis*. To aid purification and detection of the recombinant protein, the gene was expressed with a C-terminal histidine.times.6 tag from the vector pMIP12. As shown in FIG. 3, the recombinant protein was detected from cell sonicates in both the soluble and insoluble fractions by Western blot analysis using a monoclonal anti-histidine×6 POD conjugated antibody. The recombinant protein was clearly recognized by the antibody (FIG. 3*b*) with no other signal obtained, confirming specificity for the histidine ×6 tag. The protein was further isolated from the soluble fraction by $Ni^{+2}$-affinity chromatography followed by elution with imidazole as described above. Recombinant protein could be seen in the 250 mM imidazole elution in SDS-PAGE gels with Coomassie Blue staining (see FIG. 3*a*). Western blot analysis showed the 250 mM imidazole elution contained most of the protein, with a slightly smaller amount present in the 40 nm elution and none was detected in the 1 M. elution. There was a small amount of the protein still present in the flow-through, indicating that not all of the protein was bound to the column. This may be because the column was saturated with bound protein.

The apparent molecular weight of the recombinant protein from SDS-PAGE was 23 kDa, which was smaller than the calculated weight of 25.9 kDa for the full-length recombinant protein, expressed from pMIP12. This suggested that the full-length protein may have been cleaved at the N-terminus, as was predicted from its amino acid sequence, and so N-terminal sequencing of the 23 kDa band was carried out, as described above. The resulting amino acid sequence obtained, LIAGCS (SEQ ID NO. 7), was consistent with an N-terminal cleavage predicted at amino acid position 19/20 in the native protein by SignalP (see FIG. 1, amino acids 20-25). The theoretical size of the mature recombinant product based on this cleavage was 23.6 kDa and was similar to the apparent molecular mass from SDS-PAGE.

EXAMPLE 3

Materials and Methods

Western Blot Analyses of Antibodies in Animal Sera

Western blots were carried out according to methods well known to those skilled in the art. For detection of antibody to the protein of the invention from animal sera, identical amounts of recombinant protein (approximately 0.5 μg) were electrophoresed in individual lanes, alongside a molecular weight standard, on SDS-PAGE gels. The protein was transferred to PVDF or nitrocellulose membranes and stained with Ponceau S to visualise the bands. The lanes were numbered at the top of the membrane and then cut into individual strips.

For immunodetection, single strips were incubated with serum in individual small glass screw-capped bottles in 2 ml of blocking buffer. The strips remained in the bottles for washing and were then were pooled in plastic trays for incubation with appropriate secondary antibody and washing. To avoid cross-contamination, strips from different experimental groups, eg. unvaccinated and vaccinated, were pooled separately during this stage. The following secondary POD conjugated anti-IgG heavy and light chain antibodies were used: goat anti-rabbit (A 6154), donkey anti-sheep (A 3415), rabbit anti-bovine (A 7414), (Sigma, USA).

Results

Humoral Immune Responses to the Protein

To investigate immune responses to the protein of the invention, Neoparasec-vaccinated animals were used in the first instance. It was hypothesised that vaccinated animals would make an immune response to antigens possessed by the bacteria in the vaccine. In this respect, they may be similar to infected animals and therefore could be used to evaluate the immunogenicity of the protein of the invention. *M. ptb* vaccinated cattle and sheep have similarly been used to evaluate various mycobacterial proteins (Valentin-Weigand & Moriarty, 1992; Koets et al., 1999; 2001).

Serum samples from Neoparasec-vaccinated and naturally infected sheep were used in individual immunoblot assays to determine their humoral response to the protein of the invention. A high level of antibody to the protein of the invention was produced by 10 of the 11 Neoparasec-vaccinated sheep in Western blots analyses, demonstrating the protein was immunogenic, as shown in FIG. 4. There was a very faint band produced by sera from three of the sheep (507, 578 and 560) prior to vaccination and also in two naïve animals (599 and 569). Control sera from the remaining animals prior to vaccination and from unvaccinated control animals did not react with the protein (not all are shown).

To investigate if antibody to the protein of the invention was present in naturally infected animals, Western blots were probed with sera from sheep and cattle belonging to flocks and herds known to have Johne's disease present. Results with sheep sera are shown in FIG. 5. A total of five of 14 sheep had antibody to the protein of the invention. Antibody to the protein of the invention was detected in two of the five sheep with confirmed Johne's disease and in two sheep that showed no evidence of Johne's disease. A weak band was produced with one animal (26) that had a single suspicious lesion without acid-fast organisms in an examined lymph node but was not confirmed as having Johne's disease. Immunoblots were repeated several times with consistent results.

Figure 6:
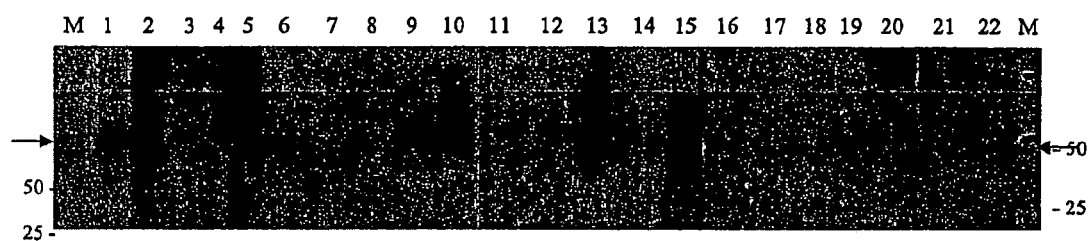

FIG. 6 shows the results of Western blot analysis using cattle sera. A summary of the results for serum ELISA, faecal culture and Western blot analysis is shown in Table 1. Antibody to the protein of the invention was present in sera from 11 of 13 preclinically infected cattle that were positive on at least one previous faecal culture. A variety of strong and weak bands were produced. Three of the four cows that were positive on all ELISA and faecal culture tests (24, 144 and 49 but not 2) also produced major bands with the protein of the invention. Two preclinically infected cows (181 and 68) did not have detectable antibody to the protein of the invention and were also negative on the last ELISA and previous faecal culture. However, other animals with similar test results, such as 58 and 34, produced strong bands with the protein of the invention. Antibody to the protein was present in four preclinically infected cows (327, 517, 58, 115) that were negative on all three serum ELISA tests. Antibody to the protein was also present in both clinically affected cows (27 ands 25). Cow 27 produced a very strong band with the protein of the invention. Of the six cows that were negative on all ELISA tests and faecal cultures, one (53) produced a weak band with the protein of the invention.

TABLE 1

Summary of results for detection of M. ptb by serum ELISA, faecal culture and Western blot analysis

| Animal # | ELISA 1 | ELISA 2 | ELISA 3 | Faecal culture 1 | Faecal culture 2 | protein |
|---|---|---|---|---|---|---|
| 24 | + | + | + | + | + | + |
| 2 | ND | + | + | + | + | + |
| 275 | + | − | + | + | + | + |
| 144 | + | + | + | + | + | + |
| 327 | − | − | − | + | + | + |
| 181 | + | + | − | + | − | − |
| 115 | − | − | − | − | + | + |
| 34 | − | + | − | + | − | + |
| 49 | + | + | + | + | + | + |
| 517 | − | − | − | + | + | + |
| 168 | ND | − | + | + | + | + |
| 58 | − | − | − | + | − | + |
| 68 | − | − | − | + | − | − |
| 27# | ND | ND | ND | ND | ND | + |
| 25* | ND | ND | ND | ND | ND | + |
| 211 | − | − | − | − | − | − |
| 132 | − | − | − | − | − | − |
| 193 | − | − | − | − | − | − |
| 97 | − | − | − | − | − | − |
| 174 | − | − | − | − | − | − |
| 53 | − | − | − | − | − | + |

Serum ELISA and faecal culture were carried out and interpreted as positive or negative by AgResearch, Wallaceville, Lower Hutt, New Zealand. Sera and faecal culture tests were done in six-monthly intervals. Sera used for Western blot analysis was from the last collection date, corresponding to ELISA 3.
ND = not done
*Johne's disease diagnosed on clinical signs and gross pathology
Johne's disease diagnosed on clinical signs and acid-fast organisms in faeces

EXAMPLE 4

Materials and Methods

IFN-γ Assays

IFN-γ assays were performed using the whole blood Bovigam™ ELA bovine interferon test, which is suitable for the detection of ovine IFN-γ. The test was performed as per the manufacturer's (Commonwealth Serum Laboratories, Australia) instructions, with some modifications. Briefly, blood samples were collected in lithium heparin tubes and processed within 4 hours of collection.

For each antigen to be tested, 1 ml aliquots of blood were dispensed into 24-well tissue culture hays. Routinely, antigens were tested in duplicate. Each antigen was added in a standard volume of 67 µl to the blood aliquots and mixed for 5 min on a rotating platform shaker. The trays were then incubated 22 h at 37° C. in a humidified atmosphere with 5% $CO_2$. From each blood/antigen aliquot, 200 µl of plasma was harvested and stored at −20° C. in 96-well plates for subsequent testing. The plasma samples were assayed singly for IFN-γ using Bovigam™ EIA plates according to the manufacturer's instructions. Absorbance readings were carried out on a MAXline, Vmax® (Molecular Devices Corp., USA) kinetic microplate reader at 450 nm.

Johnin PPD or Avian PPD (Commonwealth Serum Laboratories, Australia) was used at 12.5 µg/n as a positive control for specific stimulation. PBS was included as a negative control. For all assays, the non-specific T-cell stimulator concavalin A (Sigma, USA) was included for all animals at 20 µg/ml to check cell viability.

Results were expressed as "corrected" absorbance at 450 nm. For duplicate wells, this was defined as the average $A_{450\ nm}$ of the stimulated wells (Avian or Johnin PPD or protein of the invention) minus the average $A_{450\ nm}$ of the PBS control wells. For single the protein of the invention stimulated wells, this was defined as the $A_{450\ nm}$ of the stimulated well minus the average $A_{450\ nm}$ of the PBS control wells. Differences between groups were calculated by the Mann-Whitney test. The software package InStat 2.01 (GraphPad Software Incorporated, USA) was used for statistical analysis.

Results

Cell-mediated Immune Responses to the Protein of the Invention

Figure 7:
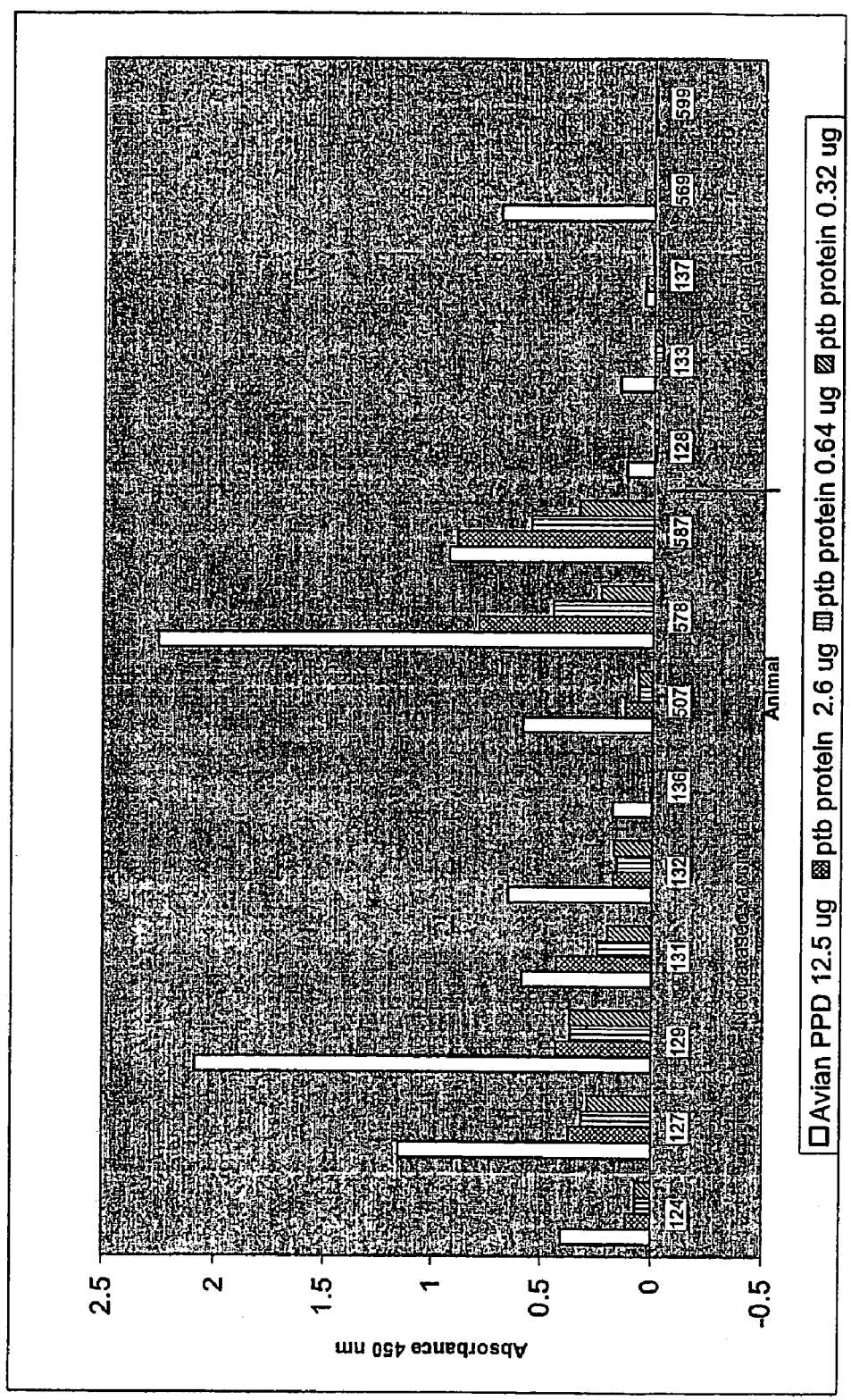
FIG. 7 shows IFN-γ induction using $Ni^{+2}$-affinity-enriched protein in Neoparasec-vaccinated sheep blood. Whole blood was incubated with 12.5 μg/ml Avian PPD in duplicate wells and 2.6 μg/ml, 0.64 μg/ml and 0.32 μg/ml $Ni^{+2}$-affinity enriched protein, in single wells. IFN-γ assays were performed as described. Results were expressed as "corrected" absorbance at 450 nm. For Avian PPD, this was defined as the average $A_{450}$ nm of the Avian PPD-stimulated wells minus the average $A_{450\ nm}$ of the PBS control wells for that animal. For each protein concentration, this was defined as the $A_{450\ nm}$ of the protein-stimulated well minus the average $A_{450\ nm}$ of the PBS control wells for that animal. There was a significant difference ($p<0.01$) in the IFN-γ responses to the protein of the invention at all three concentrations between the Neoparasec vaccinated and unvaccinated group.

To investigate if recombinant protein could stimulate cell-mediated immune (CMI) responses in Neoparasec-vaccinated animals, whole blood IFN-γ assays were carried out. In the first instance, $Ni^{+2}$-affinity enriched recombinant protein was tested in single wells in three different concentrations (2.6 µg, 0.64 µg and 0.32 µg). Results are shown in FIG. 7. There was a significant difference (pc<0.01) between the Neoparasec-vaccinated and unvaccinated group in the IFN-γ responses to protein of the invention at all three concentrations. Eight of the nine vaccinated animals showed IFN-γ production to all three concentrations of protein, often in a concentration-dependent manner. Animal 136 had very low IFN-γ production to protein and to Avian PPD. The low response to Avian PPD was consistent in this animal over the previous five months of testing (data not shown). None of the unvaccinated animals had notable IFN-γ responses to the protein of the invention, however, three of these animals (128, 133, 569) had comparatively large responses to Avian PPD, especially animal 569. Reactions of control animals to Avian PPD were not uncommon and appeared occasionally in various animals during testing over the previous five months (data not shown).

Figure 8:
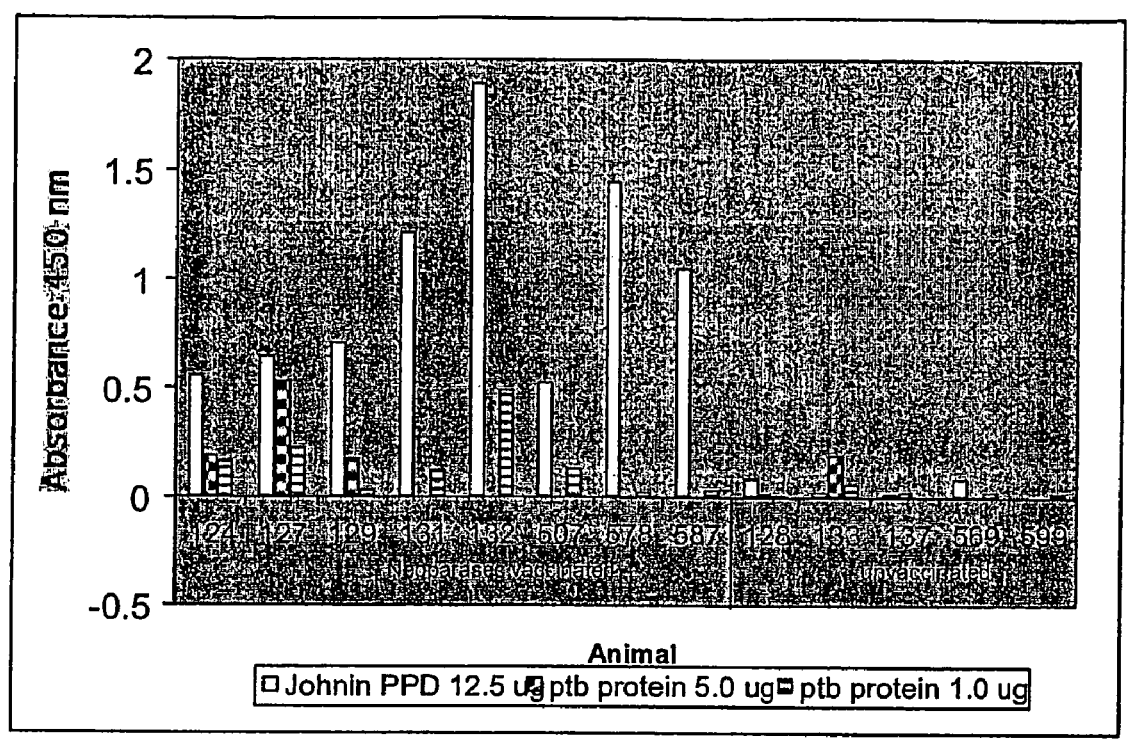
FIG. 8 shows IFN-γ induction by purified recombinant protein in Neoparasec-vaccinated sheep blood. Whole blood was incubated in duplicate wells with 12.5 μg/ml Johnin PPD and 1 μg/ml size-exclusion purified protein of the invention. To demonstrate a concentration-dependent response, Neoparasec vaccinated animals 124, 127 and 129 and unvaccinated animals 128, 133 and 137 were similarly tested with 5 μg/ml purified protein. PBS was included as a negative control in duplicate wells. IFN-γ assays were performed as described. Results were expressed as "corrected" absorbance at 450 mn, defined as the average $A_{450nm}$ of the stimulated wells minus the average $A_{450nm}$ of the PBS control wells for that animal.
Figure 9:
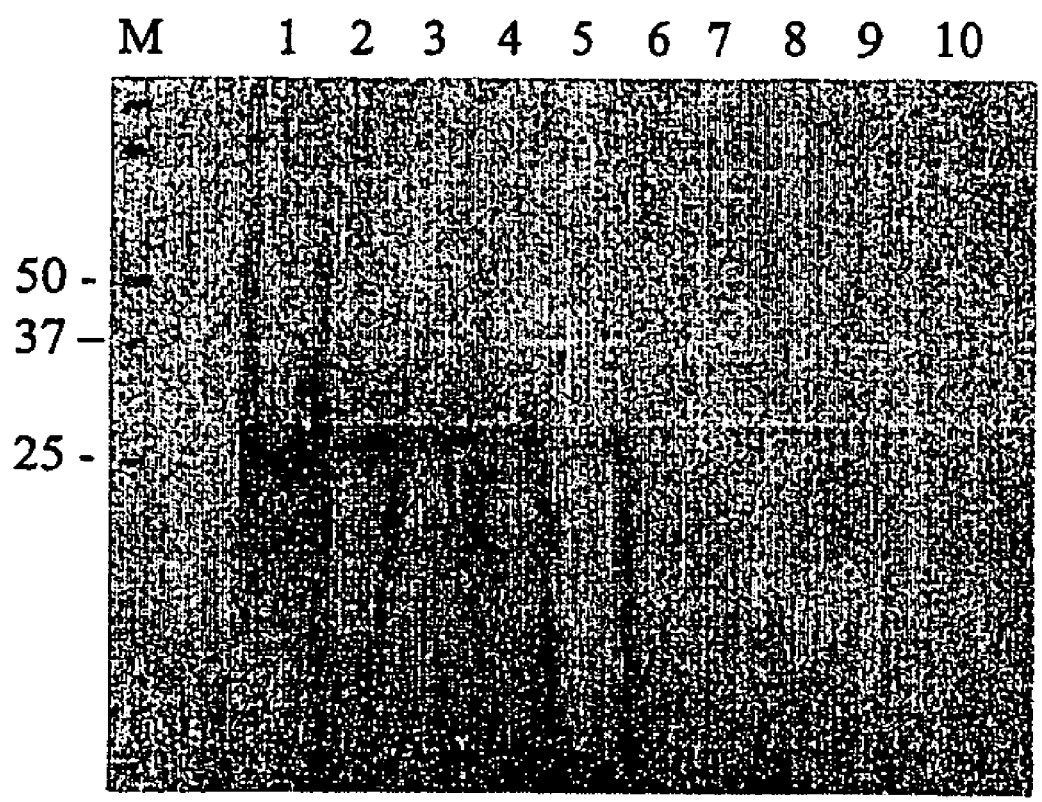
FIG. 9 shows detection of antibody to the protein of the invention from sheep vaccinated with *M. ptb* strain 316F culture filtrate. Western blots of recombinant protein were individually incubated with 1:500 dilution of serum as described. Anti-sheep IgG POD conjugated antibody was used at 1:40,000 dilution. Blots were developed by chemiluminescent detection. Lane M molecular weight standard (kDa); lanes 1 to 5, one month post-vaccination animals 571, 513, 514, 512 and 551, respectively; lanes 6 to 10, pre-vaccination, same animals.
Figure 10:
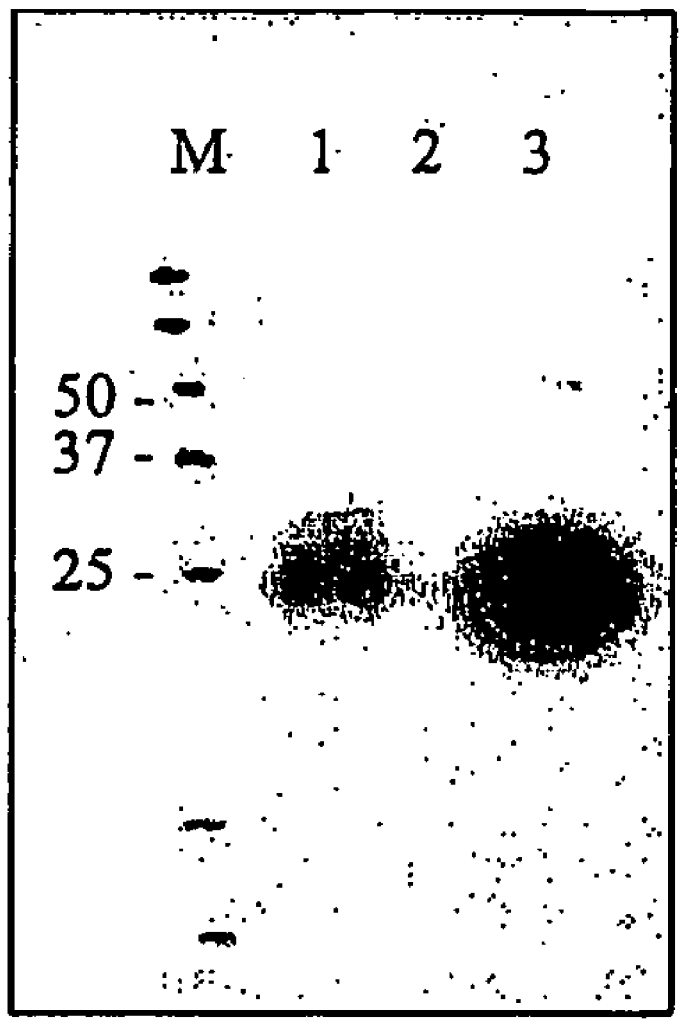
FIG. 10 shows western blot detection of rabbit antibody raised to the protein of the invention $Ni^{+2}$-affinity enriched recombinant protein was electrophoresed in SDS-PAGE gels and transferred to PVDF membranes for subsequent immnunodetections with the following sera: lane 1, serum from rabbits immunized with the protein of the invention (1:1,000); lane 2, naïve rabbit serum (1:1,000); lane 3, control anti-histidine×6 POD conjugated antibody (1:500). Lane M, molecular weight standard (kDa). Secondary anti-rabbit IgG POD conjugated antibody was used at 1:20,000. Blots were developed using chemiluminescent detection.
Figure 11:
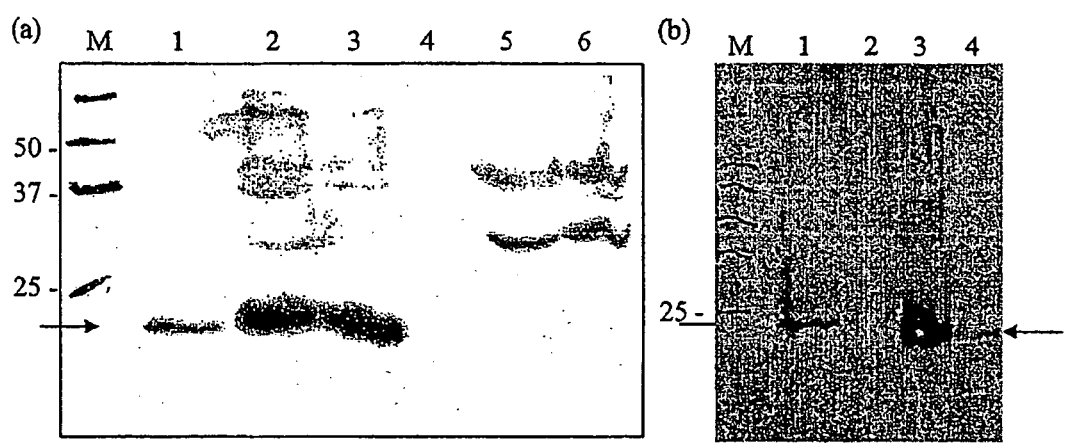
FIG. 11 shows detection of native protein of the invention in Western blots of *M. ptb* strain 316F cell fractions and comparison to recombinant protein using rabbit antibody raised to the protein of the invention. (a) *M. ptb* cell fractions. Lane M, molecular weight standard (krDa); lane 2, 10 μl (0.5 mg) of 200 fold concentrated culture filtrate; lane 3, 10 μl of equivalent 200 fold concentrated soluble cell lysate fraction; lane 4, 10 μl of equivalent 200 fold concentrated insoluble cell fraction. (b) Native protein in *M. ptb* culture filtrate and recombinant protein from *M. smegmatis*. Lane M, molecular weight standard (kDa); lane 1, 5 μg culture filtrate; lane 2, 5 μg culture media only; lane 3, 1 μg $Ni^{+2}$-affinity purified recombinant protein from *M. smegmatis* lysate; lane 4, 0.1 μg $Ni^{+2}$-affinity purified recombinant protein from *M. smegmatis* lysate, incubated with 1:500 dilution anti-histidine×6 POD conjugated antibody (control). Rabbit sera against the protein of the invention was used at 1:1,000 dilution. Secondary anti-rabbit IgG POD conjugated antibody was used at 1:20,000 dilution. Blots were developed using chemiluminescent detection as described. Arrows indicate the location of the protein of the invention.

To demonstrate that the immunologically active component in the $Ni^{+2}$-affinity preparation was the protein of the invention, the protein was purified by size-exclusion chromatography and tested for its ability to stimulate IFN-γ production in whole blood. Results are shown in FIG. 8. There was a significant difference p<0.05) in the IFN-γ responses to 1 μg of the protein of the invention between the vaccinated and unvaccinated group, despite the low responses of animals 578 and 587 in the vaccinated group and the notable response in animal 133 in the unvaccinated group. Animal 136 was not included in the assay because of its consistently poor response to Avian and Johnin PPD. To see if the IFNI production to the protein of the invention was concentration-dependent, three vaccinated animals were chosen from Mob 1, along with three unvaccinated animals for testing using 5 μg of purified protein. Only three animals from each group were tested due to limited amounts of purified protein. Two animals in the vaccinated group had evident concentration-dependent responses to the antigen and the third had a slight concentration-dependent response.

EXAMPLE 5

Localization of the Protein of the Invention in *M. ptb*

An indirect approach to investigate whether the protein of the invention is exported in its native host, *M. ptb*, was to determine if animals vaccinated with *M. ptb* strain 316F culture filtrate produced antibody to the protein.

Materials and Methods

The techniques used herein were as described in Example 4 above.

Results

Detection of the Protein with Serum from Sheep Vaccinated with *M. ptb* Strain 316F Culture Filtrate Serum samples from *M. ptb* culture filtrate-vaccinated sheep were used to probe individual Western blots of recombinant protein. Results are shown in FIG. 9.

All five vaccinated animals had antibodies to the antigen at one month post-vaccination. Antibody was not present prior to vaccination

EXAMPLE 6

Localization of the protein in *M. ptb*

A direct approach to investigate whether the protein of the invention is exported in its native host, *M. ptb*, was to determine its location in Western blots of culture filtrate fractions using rabbit antibody raised to the protein.

Materials and Methods

Preparation of the Protein for Immunisation

The protein of the invention was prepared for immunization by transferring approximately 0.05 mg of $Ni^{+2}$-affinity enriched recombinant protein onto nitrocellulose membrane. The membrane was stained with Ponceau S and the protein band was excised, destained and air-dried. The blot was then fragmented inside a microfuge tube with the aid of a sterile scalpel blade. To this, approximately 300 μl of PBS was added and the material was further fragmented until it could pass through an 18 gauge, 1½" needle. Five hundred microlitres of Freund's incomplete adjuvant (F 5506, Sigma, USA) was added and the mixture was passed through the needle several times before being injected.

Rabbit Immunisation Protocol

Adult New Zealand White rabbits were individually housed under standard conditions in outdoor hutches by Agricultural Services, Massey University, Palmerston North, New Zealand. Injection of prepared antigen was done subcutaneously in the mid-scapular skin fold of one rabbit. This was repeated *approximately three weeks later. To check for antibody production, 5 ml of venous blood was collected from the external ear by a scalpel nick three weeks after the second injection. Serum was harvested from the clotted blood after centrifugation at 3,000×g for 15 min. At the same time, serum was similarly collected from a naïve rabbit for use as control serum. The sera were aliquotted and stored at −20° C. Following confirmation of antibody production, the rabbit was exsanguinated and serum was harvested as above Results Production of Rabbit Antibody Raised to the Protein and Detection of the Protein in Cellular Fractions To determine the cellular localization of the native protein of the invention in *M. ptb* strain 316F, rabbit antibody was raised to recombinant protein. As shown in FIG. 10, the anti-serum recognized recombinant protein on Western blots. Naive rabbit serum did not recognize the protein. The serum was used to probe Western blots of equivalent amounts of *M. ptb* strain 316F culture filtrate. Results are shown in FIG. 11. A single band of apparent molecular weight 24.2 kDa was detected in the culture filtrate, which was slightly larger than the molecular weight of 22.3 kDa calculated for the mature native protein based on its amino acid composition. This band was also present in greater intensity in both the soluble and insoluble cell preparations. Several other weak bands of higher molecular weight were produced in the soluble and insoluble cell fractions with the naive and recombinant protein-immunized rabbit sera Comparison to $Ni^{+}$-affinity chromatography prepared recombinant protein produced from *M. smegmatis*, previously shown to migrate with an apparent molecular weight of 23 kDa, confirmed native protein migrated slightly slower than recombinant protein.

EXAMPLE 7

To determine if sequences related to the gene encoding the protein of the invention existed in other mycobacterial species, nucleic acid database searches, PCR and Southern blot analyses were carried out Materials and Methods PCR Amplification of the Protein-encoding ORF from Genomic DNA PCR amplifications were carried out on mycobacterial genomic DNA using the primer pairs 1pp27-fBam and 1pp27-rKpn. The reactions were carried out in 20 μl using Taq DNA polymerase. Template DNA consisted of 2 μl of a 1:50 dilution of purified DNA or, alternatively, single bacterial colonies were added directly to the PCR mixture.

Southern Blotting and Hybridizations

Approximately 1 μg of restriction endonuclease-digested genomic DNA fragments were electrophoresed in 0.7% agarose gels and transferred to nylon membranes (Biodyne B, Gelman, Pall Corporation, USA) by capillary transfer using standard procedures (Sambrook et al., 1989). The DNA was fixed to the membrane by exposure to UV light for 4 min using a Bio-Rad Gel Doe 2000 transilluminator (Bio-Rad, USA). Fixed membranes were prehybridized in heat-sealed plastic bags with: DIG Easy Hyb buffer (Roche Molecular Biochemicals, Germany) at 42° C. for 2 h with constant shaking in a Hot Shaker water bath (Bellco Biotechnology, N.J., USA). Hybridization was done in the same buffer at 2.5 ml/100 cm$^2$ with 25-50 ng/ml of denatured DIG-labeled probe DNA at 40° C. for 18 h. The hybridized membranes were washed 2.times.5 min in 2×SSC, containing 0.1% (w/v) SDS at room temperature, followed by 2×5 mm washes in 0.7×SSC containing 0.1% (w/v) SDS at 68° C. with constant shaking. Immunodetection of hybridized probe was achieved using the DIG system (Roche Molecular Biochemicals, Germany). Briefly, washed membranes were incubated in 1 ml/cm.sup.2 blocking solution (Roche Molecular Biochemicals, Germany) for 60 min at room temperature with shaking. The blocking solution volume was reduced to 20 ml/100 cm$^2$ and anti-DIG antibody conjugated to alkaline phosphatase (Roche Molecular Biochemicals, Germany) was added to a final dilution of 1:10,000 according to the manufacturer's recommendations. The blots were developed by chemiluminescence with CSPD or CPD-Star substrate (NEN, MA, USA). The developed blots were exposed to radiographic film (BioMax MR, Kodak, USA) for 5 min to 18 h, depending on signal intensity, in the presence of a single intensifying screen (Kodak Lanex Regular, Kodak, USA). Film was developed in an automated processor (Kodak RP X-OMAT Processor Model M6B).

DNA Probe Preparation

All probes were labeled by the incorporation of DIG-labeled dUTP (DIG-11-dUTP, Roche Molecular Biochemicals, Germany) during PCR. DIG-11-dUTP (1 573 152, Roche Molecular Biochemicak, Germany) was added to a final concentration of 20 µM in a reaction volume of 50 l and dTTP was adjusted to a final concentration of 80 µM. All other deoxynucleoside triphosphates were added to 100 µM. To estimate the purity and yield of DIG-labeled product, approximately 2 µl of the reaction was electrophoresed in agarose gels alongside a mass ladder for quantitation (10068-013 Low Mass DNA Ladder, Life Technologies Inc., USA). Due to the presence of DIG, the PCR products routinely appeared larger than unlabeled products. For quantitation of DIG-incorporation in probes, side-by-side filter spot tests, ranging from 0.01 pg to 10 pg, were carried out as per the manufacturer's recommendations. Labeled PCR products were stored at −20° C. until used for hybridization.

Results

Figure 12:
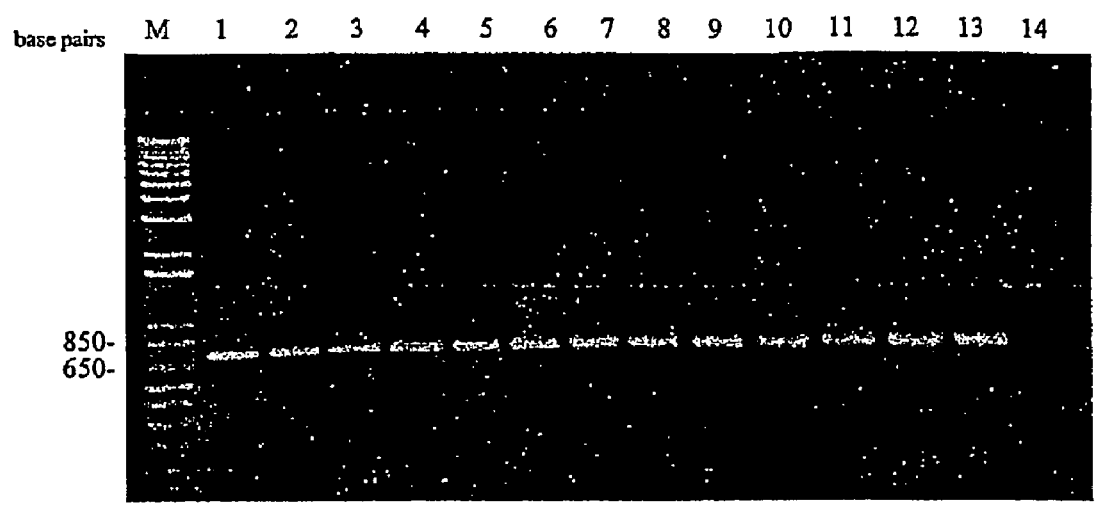
Figure 13:
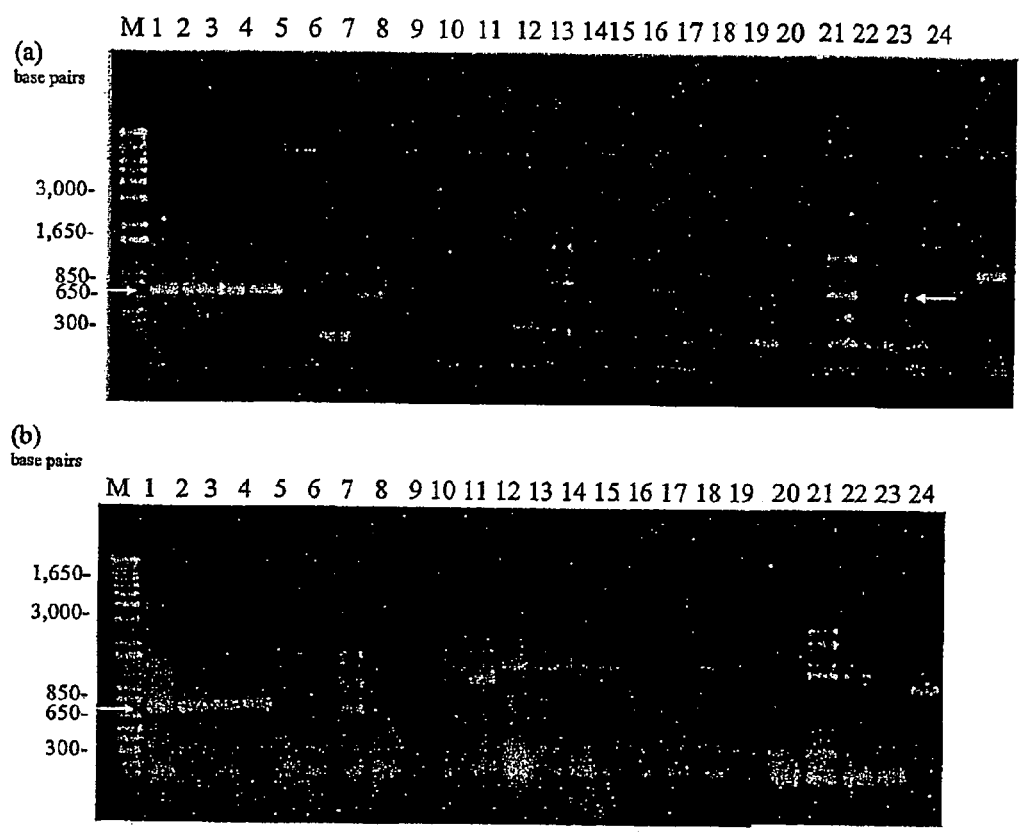
Figure 14:
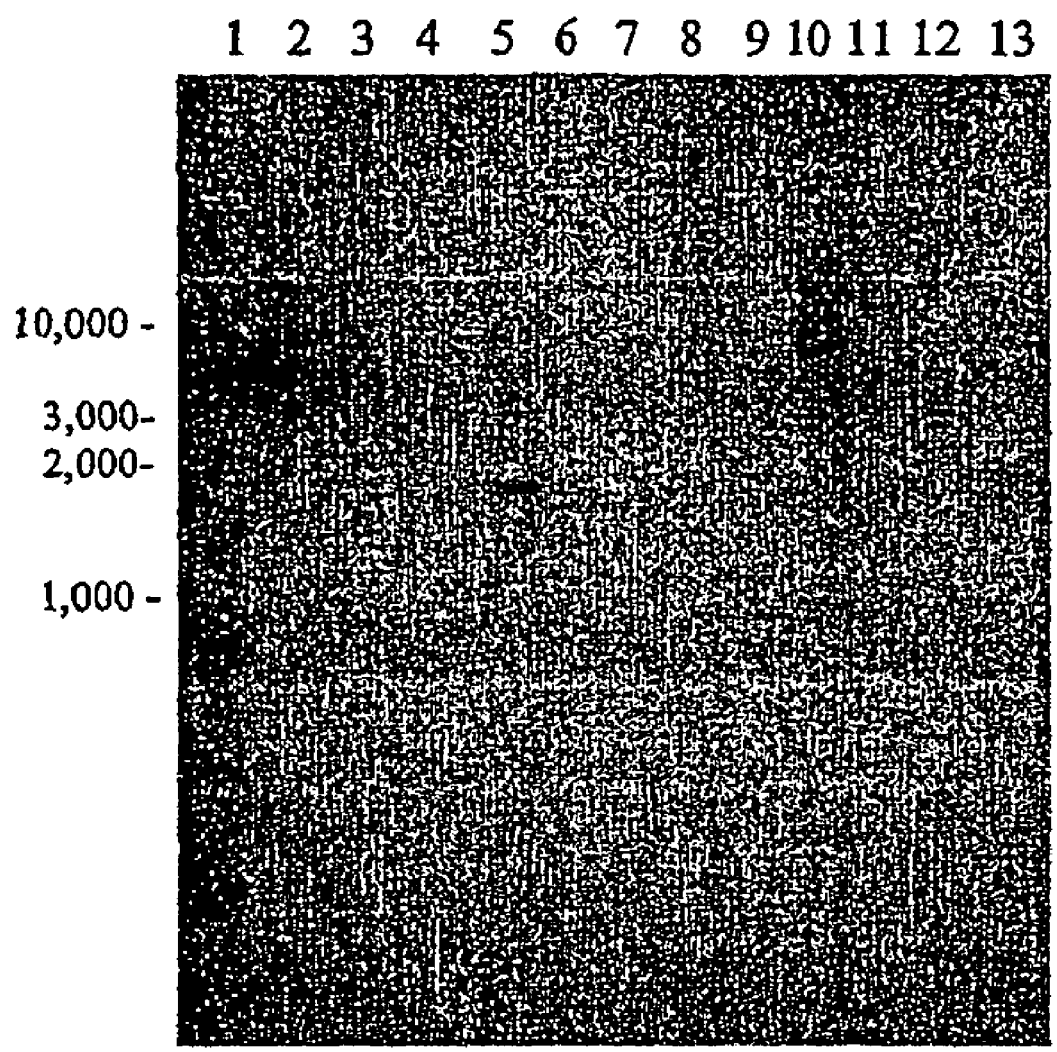

PCR Amplification of the Gene Encoding the Protein from *Mycobacterium* Species and Strains To determine if the gene encoding the protein of the invention was present in other *M. ptb* strains, several isolates representing five IS900 RFLP types (Collins et al., 1990) were used in PCR analyses. The results are shown in FIG. 12. The expected 725 base pair product was amplified from all 13 isolates.

To investigate the species distribution of the gene encoding the protein of the invention within the genus *Mycobacterium*, PCR reactions were carried out with a limited number of mycobacterial species, including two strains of *M. ptb* and 11 strains from the *M. tuberculosis* complex. Primers 1pp27-fBam and 1pp27-rKpn were used. Amplification of the genus-specific 16S rRNA gene was carried out in parallel for all DNA species and served as a positive control for the reactions. Annealing temperatures of 55° C. and 62° C. were employed (the calculated Tm of the primers was 66° C. in 50 mM NaCl). Results are shown in FIG. 13. PCR products of the expected size (725 base pairs) were amplified from both of the *M. ptb* isolates as well as *M. scrofulaceum* and *M. intracellulare* using both annealing temperatures. The only other product of the expected size for the gene of interest was produced at 55° C., in the *M. tuberculosis* complex strains (FIG. 13*b*; lanes 12-22), however this product was very weak and was not produced at 62° C. A major band it 250 base pairs was produced with *M. terrae* at 55° C., however this product was not produced at 62° C. Various weak products were amplified from several of the other species, but none of these were produced with consistency at both annealing temperatures.

Southern Blot Detection of Gene of Interest in *Mycobacterium* Species and Strains Southern blot analyses were performed with BamHI-digested genomic DNAs from 13 *Mycobacterium* spp. The ORF encoding the protein of the invention was used as probe and was labeled by incorporation of DIG-dUTP during PCR using the primers 1 pp27-fBam and 1pp27-rKpn. FIG. 14 shows the probe hybridized strongly to a single band, approximately 2,200 base pairs in length from *M. ptb* 316F and a slightly larger band of 2,300 base pairs from *M. ptb* ATCC 53950. The probe also hybridized weakly to a 1,000 base pair band from *M. intracellularae*. Upon overnight exposure (data not shown), a weak band at approximately 10,000 base pairs was present in *M. marinum, M. terrae, M. pheli* and *M. kansasii*. Hybridization was not detected with *M. bovis, M. tuberculosis*, or *M. bovis* BCG.

EXAMPLE 8

To enable ease of production of the protein of the invention in greater quantities, an expression system utilizing *E. coli* was developed. The protein of the invention so produced was used in a vaccination trial to analyse it's ability to engender an immune response.

Materials and Methods

Animals and Handling

The ovine model consisted of 17, 8 month old, Romney wether (castrated male) lambs. All vaccinations were administered subcutaneously to the right hand side of the neck using 0.6 mm×12 mm needles. Animals vaccinated with protein of the invention were kept under observation for 1 hr following vaccination, and then checked 3 hrs post vaccination to verify that there were no adverse reactions to the recombinant vaccine.

Construction of pPet22 pPET22 is pET14b (Novagen) containing the gene sequence encoding the protein of the invention devoid of the first 57 bases that encode the secretion signal. The 648 bp sequence was obtained from pMIP12 by PCR amplification using the primers P22-SF (5'-GGGAATTCCATATGTTGATCGCCGGCTGCTCGTCGGG C-3', SEQ ID NO. 8), and P22-SR (5'-GGGAATTCCATATGTCACGAGCTCA CCGGGGGCTTGGTG-3', SEQ ID NO. 9), with Pfu Turbo DNA polymerase (Strategene).

The amplified product containing NdeI restriction sites was purified from an agarose gel using the QIAquick PCR purification protocol. Following digestion with NdeI, the fragment was ligated into NdeI digested pET14b and the resulting plasmid was used to transform *E. coli* BL21-CodonPlus cells (Strategene) using standard procedures.

Affinity Purification and Concentration of Recombinant Protein

Recombinant protein of the invention was isolated from the induced *E. coli* strain BL21-CodonPlus containing the plasmid pPET22 (i.e. the expression strain) using the materials and methods provided by the ProBond purification system version F (Invitrogen, Carlsbad Calif., USA).

In brief, cells were lysed under protein denaturing conditions by resuspending cell pellets in a buffer containing 6 M. guanidine hydrochloride, 20 mM sodium phosphate, and 500 mM sodium chloride and with a pH of 7.8. RNA and DNA were sheared by sonication to reduce viscosity, and this was followed by centrifugation at 3,000×g for 15 minutes to remove insoluble debris. The lysate supernatant was mixed with the ProBond resin. The mixture was then centrifuged to separate the resin from the lysate. The lysate was removed, and the resin was washed several times with the following wash buffers:
1. Denaturing binding buffer; 8 M. urea, 20 mM sodium phosphate 500 mM sodium chloride, pH 7.8,
2. Denaturing wash buffer 6.0; 8 M. urea, 20 mM sodium phosphate 500 mM sodium chloride, pH 6.0,
3. Denaturing wash buffer 5.3; 8 M. urea, 20 mM sodium phosphate 500 mM sodium chloride, pH 5.3.

Following each washing step, the wash mix was centrifuged to separate the resin from the wash buffer. The samples were then eluted by resuspending the resin several times in Denaturing elution buffer; 8 M. urea, 20 mM sodium phosphate 500 mM sodium chloride, pH 4.0.

The wash and elution fractions were analysed by SDS-PAGE to determine which fractions contained purified protein of the invention. Fractions containing purified protein of the invention were then pooled together and dialyzed against PBS and urea by incrementally reducing the concentration of urea in the dialysis buffer by 1 M each time the buffer was changed until urea concentration was below 0.1 mM.

Protein of the invention was concentrated by ultrafiltration, and sterility was verified by inoculating blood agar plates with the protein solution (~100 µl of concentrated protein solution streaked across a third of a blood agar plate) and incubating for up to 1 week at 37° C. Samples showing no bacterial growth were considered suitable for ovine testing.

Concentrated protein samples were also submitted to the Institute of Environmental Science & Research Limited, New Zealand for determination of endotoxin quantities using the LAL (Limulus Amoebocyte Lysate) test (Associates of Cape Cod Inc. USA).

Vaccination Trials

A total of 17 sheep were used for the protein of the invention vaccination trial testing (Table 2). Six animals were vaccinated with 1 ml of the commercially available Neoparasec vaccine (Merial Ltd.). Five animals were vaccinated with 0.8 mg of the recombinant protein of the invention mixed approximately 1:1 (v/v) with Neoparasec adjuvant for a total volume of 2 ml. Six animals were used as an unvaccinated control group.

TABLE 2

| Vaccine | Vaccination Date | Sheep No. | Weight (kg) | Group weight average (kg) |
| --- | --- | --- | --- | --- |
| Control group | N/a | | | 37.1 |
| none | | 808 | 39.1 | |
| none | | 823 | 39.3 | |
| none | | 830 | 39.4 | |
| none | | 834 | 37.9 | |
| none | | 863 | 31.9 | |
| none | | 869 | 34.7 | |
| Neoparasec group | Jan. 30, 2003 | | | 38.2 |
| Neoparasec | | 811 | 36.2 | |
| Neoparasec | | 813 | 43.9 | |

TABLE 2-continued

| Vaccine | Vaccination Date | Sheep No. | Weight (kg) | Group weight average (kg) |
| --- | --- | --- | --- | --- |
| Neoparasec | | 817 | 38.7 | |
| Neoparasec | | 819 | 37.5 | |
| Neoparasec | | 821 | 37.1 | |
| Neoparasec | | 854 | 35.8 | |
| Recombinant protein group | Apr. 16, 2003 | | | 38.1 |
| protein | | 820 | 37.2 | |
| protein | | 825 | 39.7 | |
| protein | | 828 | 36.1 | |
| protein | | 829 | 36.1 | |
| protein | | 848 | 41.3 | |

Western Blotting

Purified protein of the invention (133 µg protein/ml) was added at 3 µl per well on 15% SDS-PAGE gels. Following electrophoresis, the protein on the gel was blotted to a PVDF membrane using a Trans-Blot SD Semi-Dry Transfer Cell (BioRad, USA). The membranes were stained with Ponceau S to verify that protein transfer had taken place. The membranes were then destained with deionized $H_2O$, and blocked overnight in 5% (w/v) skim milk at 4° C.

Following blocking thin strips corresponding to lanes of the original gel were cut and placed separately in plastic trays. Serum samples from sheep vaccinated with the protein of the invention, Neoparasec and non-vaccinated control sheep were added separately to a membrane strip after diluting 1:500. These strips were incubated for 1 hr at room temperature followed by washing several times to remove any unbound serum. The strips were then incubated in peroxidase conjugated anti-sheep IgG secondary antibody diluted 1:40, 000. The strips were washed several times to remove any unbound antibody, and SuperSignal West Femto Maximum Sensitivity Substrate (Pierce Scientific, USA) was added to the membrane, followed by exposure to BioMax scientific imaging film (Kodak, 20 USA) for time periods of 5, 15, 30, 60, and 180 seconds following which the film was immediately developed.

Measuring IFN-γ Production from Sheep Vaccinated with Protein of the Invention

Five weeks following vaccination with the protein of the invention, each sheep had approximately 8 ml of blood collected into a 10 ml Vacutainer tube containing lithium heparin (Beckton Dickinson, UK). Also at this time, two sheep that had received Neoparasec vaccine and two that were unvaccinated were also bled.

Duplicate 1 ml aliquots of each sample were incubated for 20 h with these antigens at the given concentrations: PBS (negative control), PPD A 12.56 µg/ml, protein of the invention 10 µg/ml, and a single aliquot of Concavalin A-Con A (positive control) 20 µg/ml. Following incubation, approximately 200 µl of the cytokine containing plasma was removed and placed in a 96 well tray: 50 µl of this plasma was then used to perform a Bovigam Tm Bovine Gamma Interferon Test, (CSL, Australia, batch no: 0300-07001).

ELISA for the Quantification of Serum Antibodies Specific to the Protein of the Invention A protein of the invention-adsorbed enzyme-linked immunosorbent assay (ELISA) was used to measure the level of antibodies (5 weeks post vaccination) that had been raised specifically against the protein of the invention.

The recombinant protein of the invention was purified under denaturing conditions using a nickel affinity column (ProBond, Invitrogen, Calif., USA) according to manufacturer's instructions. Following fiber purification through a Sephadex 75 HR 10/30 column, protein of the invention was adsorbed onto 96 well microtitre plates (Dynex Technologies Inc, Virginia, USA) at a concentration of 0.15 μg/well. Plates were blocked overnight at 4° C. with 5% (w/v) milk powder in PBS (blocking buffer) added to each well (200 μl/well) before washing 3 times with PBS containing 0.05% (v/v) Tween-20; followed by one wash with PBS.

Serum collected from Neoparasec (animals 811, 813, 817, 819, and 821), protein of the invention (animals 820, 825, 828, 829 and 848) or non-vaccinated animals (animals 808, 823, 830, 834, 863 and 869) were pre-diluted 1:200 or 1:800 in blocking buffer before being added to each well (100 μl/well) in duplicate. As a negative control (background), blocking buffer was added to wells instead of test sera Following incubation for 1 h at 37 ° C., unbound antibodies were removed by washing as previously described. Bound antibodies were detected with 100 μl/well of alkaline-phosphatase conjugated donkey anti-sheep immunoglobulin (Sigma, Virginia, USA), diluted 1:30000 in PBS and incubated for 1 h at 37 ° C. The plates were washed as described, and the reaction developed with p Nitrophenyl Phosphate (PNNP, Sigma, USA), 1 mg/ml in 10% diethanolamine buffer, pH 9.8, containing 0.5 MM $MgCl_2$.

After a 25 min incubation, measurements were obtained by reading the absorbance at $OD_{405}$ using an ELISA plate reader (Vmax, Molecular Devices Corp., California, USA). The reaction was then stopped by adding 100 μl/well of 2 M sodium carbonate solution. Mean optical densities were calculated for each duplicate sample and these were corrected by subtraction of the mean $OD_{405}$ of their respective negative control wells.

Results

Preparation of Recombinant Protein of the Invention

Affinity purified protein of the invention was made in 6 separate batches recorded as MB1 a, MB1 b, MB1c, DB1, DB2, and DB3. These were combined to yield a final volume of 4.8 ml having a protein concentration of 0.799 mg/ml. The purity of this sample was determined based on SDS-PAGE analysis of the protein samples following purification (FIG. 15).

The endotoxin test reported that the sample (MB1b) had $10^5$ EU (endotoxin units)/ml (results from Environmental Science & Research Limited, New Zealand 3/26/2003). Since 1 EU=0.1 ng endotoxin (Environmental Science & Research Limited, New Zealand), then $10^5$ EU=$10^4$ ng of endotoxin or 10 μg, and the concentration of endotoxin in the sample was 10 μg/ml or about 31 μg endotoxin/mg protein as determined using the protein assay method of Bradford.

Cell Mediated Immune Response to the Protein of the Invention

Five weeks after the vaccination blood was drawn from five animals of each group to compare protein of the invention-specific cell mediated immune responses and humoral immune responses. Using IFN-γ production as an indicator of a cell mediated response, the results (FIG. 16) demonstrate that the group vaccinated with the protein of the invention elicits a cellular immune response when stimulated in vitro with protein of the invention in four out of the 5 animals (solid black bars) as compared with the non-vaccinated sheep.

Humoral Immune Response

Western blot and ELISA were used to test for the presence of antibodies specific to the protein of the invention in the group vaccinated with the protein of the invention, as compared to the Neoparasec vaccinated and non-vaccinated groups.

Western blot analysis using serum from five animals in each of the three groups (FIG. 17) shows that 4 out of the 5 animals belonging to the group vaccinated with the protein of the invention elicited a strong humoral response against recombinant protein of the invention (animal numbers 825, 820, 828, and 829), and one had a very weak- response (number 848). 4 of the 5 Neoparasec vaccinated sheep demonstrated a strong humoral response (animal numbers 811, 813, 817, and 819), while one showed a weak response (number 821). None of the control animals gave a significant response to the protein of the invention antigen. Analysis by ELISA (see FIGS. 18 and 19) clearly demonstrates that at 5 weeks post vaccination, the animals vaccinated with Neoparasec and those vaccinated with the protein of the invention elicited a significant protein of the invention-specific antibody response. Antibody responses in some animals vaccinated with the protein of the invention matched that of the Neoparasec (positive control) vaccinees. As expected, further dilution of the antibody from 1 in 200 to 1 in 800 decreased the OD values for all the animals.

It will be appreciated that the above description is provided by way of example only and that the variations in both the materials and the techniques used which are known to those persons skilled in the art are contemplated.

What is claimed is:

1. A recombinant, purified, or isolated polypeptide comprising an amino acid sequence selected from
    (a) the sequence of SEQ ID NO: 1;
    (b) amino acids 20 to 235 of SEQ ID NO: 1;
    (c) a sequence which has greater than 95% amino acid sequence identity with SEQ ID NO: 1; or
    (d) a sequence which has greater than 95% amino acid sequence identity with the sequence of amino acids 20 to 235 of SEQ ID NO: 1.

2. The polypeptide as claimed in claim 1 wherein the amino acid sequence of the polypeptide has greater than 97% amino acid sequence identity with SEQ ID NO:1.

3. The polypeptide as claimed in claim 1 wherein the amino acid sequence of the polypeptide has greater than 99% amino acid sequence identity with SEQ ID NO: 1.

4. The polypeptide as claimed in claim 1 wherein the amino acid sequence of the polypeptide has greater than 99% amino acid sequence identity with the sequence of amino acids 20 to 235 of SEQ ID NO: 1.

5. The polypeptide as claimed in claim 1 wherein the polypeptide consists of an amino acid sequence selected from
    (a) the sequence of SEQ ID NO: 1;
    (b) amino acids 20 to 235 of SEQ ID NO: 1;
    (c) a sequence which has greater than 95% amino acid sequence identity with SEQ ID NO: 1; or
    (d) a sequence which has greater than 95% amino acid sequence identity with the sequence of amino acids 20 to 235 of SEQ ID NO: 1.

6. A kit for use in detecting the presence of *Mycobacterium avium* subspecies *paratuberculosis* comprising at least two of the following:
    a polypeptide as claimed in claim 5;
    an antibody that binds a polypeptide consisting of an amino acid sequence selected from (a) the sequence of SEQ ID NO:1 or (b) amino acids 20 to 235 of SEQ ID NO:1; or
    a reagent for determining antigen-antibody binding.

7. The polypeptide as claimed in claim 1 obtained from a bacterium.

8. The polypeptide as claimed in claim 1 obtained from *Mycobacterium avium* subspecies *paratuberculosis*.

9. The polypeptide as claimed in claim 1 obtained from a heterologous host transformed with a polynucleotide which encodes the polypeptide, wherein said host is capable of expressing said polypeptide.

10. The polypeptide as claimed in claim 9 wherein the host is *E coli*.

11. A genetic construct comprising
    (a) a promoter sequence;
    (b) an open reading frame polynucleotide encoding a polypeptide as claimed in claim 1; and
    (c) a termination sequence.

12. A host cell incorporating a construct of claim 11.

13. A vector comprising the construct as claimed in claim 11.

14. A host cell incorporating a vector as claimed in claim 13.

15. The host cell according to claim 14 wherein said vector exists within the host cell as a plasmid.

16. The host cell according to claim 14 wherein said vector is integrated into the genome of the host cell.

17. A vaccine composition comprising a polypeptide as claimed in claim 1 and an acceptable diluent, carrier, excipient, or adjuvant, said polypeptide being present in an amount sufficient to generate a protective immune response to *Mycobacterium avium* subspecies *paratuberculosis* infection.

18. A method of vaccinating against Johne's disease which comprises administering to an animal a vaccine composition as claimed in claim 17 in an amount sufficient to produce a protective response.

19. The method according to claim 18 wherein said administration is performed on a single occasion.

20. The method according to claim 18 wherein said administration is performed on more than one occasion.

21. The method as claimed in claim 18 wherein 0.1-1000 μg/Kg is administered of a recombinant, purified, or isolated polypeptide comprising an amino acid sequence selected from
    (a) the sequence of SEQ ID NO: 1;
    (b) amino acids 20 to 235 of SEQ ID NO:1;
    (c) a sequence which has greater than 95% amino acid sequence identity with SEQ ID NO:1; or
    (d) a sequence which has greater than 95% amino acid sequence identity with the sequence of amino acids 20 to 235 of SEQ ID NO:1.

22. The method as claimed in claim 21 wherein 5-500 μg/Kg of the polypeptide is administered.

23. A diagnostic composition for use in detecting the presence of *Mycobacterium avium* subspecies *paratuberculosis*, wherein said composition comprises a polypeptide as claimed in claim 1 together with one or more acceptable diluents, carriers, excipients, or adjuvants.

24. A method of prophylactically or therapeutically treating an animal against Johne's disease which comprises administering to an animal a polypeptide as claimed in claim 1 to produce a protective immunological response in the animal.

25. The method according to claim 24 which is a therapeutic method.

26. The method according to claim 24 which is a prophylactic method.

27. The method as claimed in claim 24 wherein the animal is a ruminant.

28. The method as claimed in claim 27 wherein the ruminant is a sheep.

29. A recombinant, purified, or isolated polynucleotide comprising the sequence of SEQ ID NO: 2 or a variant thereof encoding a polypeptide comprising an amino acid sequence selected from
    (a) the sequence of SEQ ID No:1;
    (b) amino acids 20 to 235 of SEQ ID NO:1;
    (c) a sequence which has greater than 95% amino acid sequence identity with SEQ ID NO:1; or
    (d) a sequence which has greater than 95% amino acid sequence identity with the sequence of amino acids 20 to 235 of SEQ ID NO:1.

30. A recombinant, purified or isolated polynucleotide with a nucleotide sequence complementary to the polynucleotide of claim 29.

31. A diagnostic composition for detecting the presence of *Mycobacterium avium* subspecies *paratuberculosis*, wherein said composition comprises a polynucleotide according to claim 29 together with one or more acceptable diluents, carriers, excipients, or adjuvants.

32. A host cell transformed with a polynucleotide of claim 29.

33. A purified or isolated antibody capable of binding a polypeptide consisting of an amino acid sequence selected from (a) the sequence of SEQ ID NO:1 or (b) amino acids 20 to 235 of SEQ ID NO:1.

34. A diagnostic composition for detecting the presence of *Mycobacterium avium* subspecies *paratuberculosis* comprising an antibody according to claim 33 together with one or more acceptable diluents, carriers, excipients, or adjuvants.

35. A method of detecting Johne's disease including preclinical Johne's disease in an animal, the method comprising contacting a sample from the animal either with a purified or isolated antibody capable of binding a polypeptide consisting of an amino acid sequence selected from
   (a) the sequence of SEQ ID NO:1 or
   (b) amino acids 20 to 235 of SEQ ID NO:1 or with a composition comprising an antibody specific to a polypeptide consisting of an amino acid sequence selected from
   (a) the sequence of SEQ ID NO:1 or
   (b) amino acids 20 to 235 of SEQ ID NO:1, and one or more acceptable diluents, carriers, excipients, or adjuvants, and detecting a polypeptide which binds to the antibody.

36. The method according to claim 35 wherein the presence of bound antibody is determined by ELISA, radioimmunoassay or Western blotting.

37. The method according to claim 35 for detecting the presence of *Mycobacterium avium* subspecies *paratuberculosis* at a preclinical phase of Johne's disease.

38. A method of detecting Johne's disease including preclinical Johne's disease in an animal comprising contacting either the animal or a sample from the animal with a polypeptide and detecting an immune response indicative of the presence of *Mycobacterium avium* subspecies *paratuberculosis*, the polypeptide consists of an amino acid sequence selected from (a) the sequence of SEQ ID NO:1 or (b) amino acids 20 to 235 of SEQ ID NO:1.

39. The method according to claim 38 wherein the response is a delayed-type hypersensitivity response.

40. The method according to claim 38 wherein said detecting comprises detecting the presence of antibodies that bind the polypeptide.

41. The method according to claim 40 wherein the detection of the presence of antibodies is by ELISA, radioimmunoassay or Western blotting.

42. The method as claimed in claim 38 wherein the animal is a ruminant.

43. The method as claimed in claim 42 wherein the animal is a sheep.

\* \* \* \* \*